(12) United States Patent
Ji et al.

(10) Patent No.: US 7,897,838 B2
(45) Date of Patent: Mar. 1, 2011

(54) METHODS FOR HIGH EFFICIENCY TRANSFORMATION AND REGENERATION OF PLANT SUSPENSION CULTURES

(75) Inventors: Lianghui Ji, Singapore (SG); Cai Lin, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 916 days.

(21) Appl. No.: 11/587,039

(22) PCT Filed: Apr. 20, 2004

(86) PCT No.: PCT/SG2004/000101
§ 371 (c)(1), (2), (4) Date: Jun. 20, 2007

(87) PCT Pub. No.: WO2005/103271
PCT Pub. Date: Nov. 3, 2005

(65) Prior Publication Data
US 2009/0165175 A1 Jun. 25, 2009

(51) Int. Cl.
*C12N 15/84* (2006.01)
*A01H 4/00* (2006.01)

(52) U.S. Cl. .............. 800/294; 800/314; 800/260; 435/427; 435/430.1; 435/431

(58) Field of Classification Search ............ None
See application file for complete search history.

(56) References Cited

U.S. PATENT DOCUMENTS

| | | | |
|---|---|---|---|
| 5,244,802 A | 9/1993 | Rangan | |
| 5,583,036 A | 12/1996 | Rangan et al. | |
| 6,483,013 B1 * | 11/2002 | Reynaerts et al. | 800/294 |
| 7,138,277 B2 * | 11/2006 | Shinozaki et al. | 435/419 |
| 2001/0026939 A1 * | 10/2001 | Rice et al. | 435/419 |
| 2002/0100083 A1 | 7/2002 | Connett-Porceddu et al. | |

FOREIGN PATENT DOCUMENTS

WO 00/34491 A2 6/2000

OTHER PUBLICATIONS

Sunilkumar et al. Plant Molecular Biology 50: 463-474 (2002).*
Hiei et al. Plant Journal 6: 271-282 (1994).*
Urushibara, S. et al., "Efficient transformation of suspension-cultured rice cells mediated by *Agrobacterium tumefaciens*," Breeding Science, vol. 51, No. 1, Mar. 2001, pp. 33-38.
Scott, R.J., et al., "Transformation of carrot tissues derived from proembryogenic suspension cells: A useful model system for gene expression studies in plants," Plant Molecular Biology, vol. 8, pp. 265-274 (1987), copyright Martinus Nijhoff Publishers—Printed in Netherlands.
McLean, B. Gail et al., "Mutants of Agrobacterium VirA That Activate vir Gene Expression in the Absence of the Inducer Acetosyringone*," The Journal of Biological Chemistry, vol. 269, No. 4, Issue of Jan. 28, pp. 2645-2651, 1994.
The Patent Office of the People's Republic of China, Notification of First Office Action (National Phase of PCT Application), Applicant: Temassek Life Sciences Laboratory Limited, Patent Agent: Lin Xiaohong, Filing No. 200480042792.3, "Methods for High Efficiency Transformation and Regeneration of Plant Suspension Cultures," (5 pages), English translation.

* cited by examiner

*Primary Examiner*—David T Fox
(74) *Attorney, Agent, or Firm*—Rothwell, Figg, Ernst & Manbeck p.c.

(57) ABSTRACT

The present invention provides methods for high efficiency plant transformation via *Agrobacterium*-mediated T-DNA conjugation to suspension-cultured cells or calli. The methods described herein employ membranes or filters as porous solid support for the co-culture of T-DNA donor and recipient.

17 Claims, 16 Drawing Sheets

METHODS FOR HIGH EFFICIENCY TRANSFORMATION AND REGENERATION OF PLANT SUSPENSION CULTURES

CROSS-REFERENCE TO RELATED APPLICATION

The present application is a national stage filing under 35 U.S.C. §371 of PCT/SG2004/000101, filed on 20 Apr. 2004, which is incorporated herein by reference.

FIELD OF THE INVENTION

The present invention relates generally to genetic engineering of plants, and, more particularly, to methods of *Agrobacterium*-mediated transformation.

BACKGROUND OF THE INVENTION

Throughout this application, various patents, published patent applications and publications are referenced. Disclosures of these patents, published patent applications and publications in their entireties are hereby incorporated by reference into this application to more fully describe the state of the art to which this invention pertains. Full bibliographic citations for the publications may be found listed in the Bibliography immediately preceding the claims.

Cotton is an economically important crop. Annual cotton fiber production contributes billions of U.S. dollars to the world's agricultural economy. While gene transformation of cotton has been possible since 1987 (Firoozabady et al., 1987), the methods used today remain very inefficient and costly due to unusually low rates of plant regeneration from the transformed cells, and low flower fertility. The lengthy regeneration process adds a further drag to the efficiency.

Several methods have been available for *Agrobacterium*-mediated transformation of a variety of cotton explants, such as cotyledons (Firoozabady et al., 1987), hypocotyls (Umbeck et al., 1987; U.S. Pat. Nos. 5,004,863 and 5,159,135; European patent publication "EP" 0 270 355), petiole (PCT publication WO 00/77230 A1) and root (PCT Pub. WO 00/53783). Improved methods for cotton plant regeneration and transformation have been reported using hypocotyl transition zones (WO 98/15622), shoot apices (WO 89/12102 and U.S. Pat. No. 5,164,310) and apical or nodal meristematic tissues (WO 97/43430). Alternatively, cotton explants can be transformed by microprojectile bombardment, for example, embryonic axes (WO 92/15675 and EP 0 531 506; McCabe and Martinell, 1993) and embryogenic suspension cultures (Finer and Mc Mullen, 1990).

Most methods cited above employ a regeneration path of somatic embryogenesis, which requires a lengthy process of initiation, maturation and germination. Transformation of somatic embryogenic callus tissues or embryogenic suspension cultures, either via *Agrobacterium*-mediated transformation (U.S. Pat. No. 6,483,013; U.S. Pat. No. 5,583,036) or particle bombardment (Finer and Mc Mullen, 1990), has substantially shortened the regeneration process. Nevertheless, transformation remains severely hampered by the unusually low conversion rate of somatic embryos to normal rooted plantlets.

Apart from regeneration, more efficient methods for delivering T-DNA into the host genome have been sought in connection with transformation of plants such as cotton. Extensive investigations have been undertaken in the understanding of *Agrobacterium* virulence and T-DNA conjugation. Today, it is well understood that before T-DNA can be delivered into the plant cells, *Agrobacterium* cells must recognize and attach themselves to the host cells through complex signaling mechanisms mediated by chemical factors secreted by the host, the production of which is induced by mechanical wounding. These chemical factors consist of a variety of phenolic compounds such as acetosyringone, sinapinic acid (3,5 dimethoxy-4-hydroxycinnamic acid), syringic acid (4-hydroxy-3,5 dimethoxybenzoic acid), ferulic acid (4-hydroxy-3-methoxycinnamic acid), catechol (1,2-dihydroxybenzene), p-hydroxybenzoic acid (4-hydroxybenzoic acid), β-resorcylic acid (2,4 dihydroxybenzoic acid), protocatechuic acid (3,4-dihydroxybenzoic acid), pyrrogallic acid (2,3,4-trihydroxybenzoic acid), gallic acid (3,4,5-trihydroxybenzoic acid) and vanillin (3-methoxy-4-hydroxybenzaldehyde) (U.S. Pat. No. 6,483,013). A constitutively expressed virG mutant protein (virGN54D) has been found to enhance *Agrobacterium* virulence and transformation efficiency. (Hansen et al, 1994). Similarly, chemical compounds, such as acetosyringone or nopaline, that stimulate *Agrobacterium* virulence, markedly increased transformation efficiency of cotton shoot tips (Veluthambi et al., 1989) and somatic embryogenic callus that was propagated on solid media (U.S. Pat. No. 6,483,013). An example is the successful transformation of a large number of fungi, which are unable to secrete *Agrobacterium* virulence inducing compounds, making acetosyringone indispensable for T-DNA conjugation (Bundock et al., 1995; de Groot et al., 1998).

Despite the many past efforts and attempts to improve transformation methods, the techniques used to date remain unproductive, time-consuming and costly. Consequently, some plants, such as cotton, fall a long way behind other major crops in the understanding of molecular mechanisms of plant development and tissue differentiation. Clearly, the current transformation techniques are inconsistent with the economic importance of cotton in particular, and a breakthrough is long overdue.

In the majority of plants, including cotton, transformation methods primarily exploit *Agrobacterium* to deliver T-DNA into host cells that are confined to a small surface area, i.e., the cut surface of explants or callus (U.S. Pat. No. 6,483,013). This greatly limits the incidence of gene transformation as the majority of host cells are not in direct contact with the T-DNA donor. As a result, only about 20-30% of explants are transformed (Firoozababy et al., 1987; Cousins et al., 1991). Previously, cell suspension cultures have been successfully transformed using a co-culture regime that was based on liquid medium in a AT-tube® or in a flask (U.S. Pat. No. 5,583,036). While no detailed rate of transformation was shown, we found the method has a similarly low transformation efficiency (FIG. 14). A major problem in the method could be the low T-DNA conjugation efficiency when co-culture was performed in rich liquid medium in which *Agrobacterium* cells may have difficulty expressing virulence genes and attaching to the plant cells that were put under constant agitation.

In contrast to explants that have been used predominantly for transformation of plants, cells in suspension cultures are present as a single cell or a small clump of cells. Currently, an efficient technique to handle and transform these materials is lacking. Recent studies have suggested that fungal cells cultured in liquid medium can be transformed when co-culture is performed on porous membranes that were laid atop semi-solid medium that had been optimized for *Agrobacterium* virulence (PCT Pub. WO 02/00896; Bundock et al., 1995; Piers et al., 1996; de Groot et al., 1998). The use of membranes or filters has a twofold advantage. It effectively filters out excessive liquid that has been carried over, collecting the T-DNA recipient and donor cells while allowing efficient diffusion of nutrients, minerals and signaling compounds between the co-culture and medium.

Finer (1988; European Pat. 0317512 B1) initiated embryogenesis in low auxin-containing liquid medium (MS salts, 15 Vitamins, 0.1 mg/l 2,4-D or 0.5 mg/l picloram, 2% sucrose) using undifferentiated calli derived from cotyledon or hypocotyl explants. The embryogenic tissues were then proliferated/maintained in similar liquid medium with a higher auxin content (5 mg/l 2,4-D). The suspension tissues thus prepared may develop into mature embryos in liquid medium if glutamine is present.

Rangan et al (U.S. Pat. Nos. 5,583,036 and 5,244,802) initiated somatic embryo formation in high auxin solid medium (1-10 mg/l) and maintained the embryogenic callus in high auxin (1-10 mg/l) liquid medium using differentiated callus derived from cotyledon, hypocotyl explants or zygotic embryos produced on solid medium. The culture contained a mixture of embryogenic cell clumps of various sizes and needed to be filtered regularly to remove larger clumps.

Trolinder and Goodin (1987) initiated embryogenesis in hormone-free liquid medium and maintained the suspension cultures in the same medium. Cells in this type of suspension culture have heterologous developmental stages and are present as large clumps that secrete darkening, growth-inhibiting compounds.

Levee, et al., (1999), and U.S. Pat. Application Publication Nos. US2002/0100083 A1, US2002/0083495 A1, and US2002/0092037 A1 refer to the use of membranes in the co-culture of pine cells.

There remains a need in the art for improved and more efficient methods of *Agrobacterium*-mediated transformation and regeneration of plants, such as cotton, maize, soybean, wheat, rice, and barley.

SUMMARY OF THE INVENTION

To overcome the problems associated with previously reported methods of plant (particularly cotton) transformation, the present invention provides methods for high efficiency plant transformation via *Agrobacterium*-mediated T-DNA conjugation to suspension-cultured cells or calli. The methods described herein employ membranes or filters as solid support for co-culture of T-DNA donor and recipient. In particular, the present invention provides a method for producing a transgenic plant, which comprises providing a pro-embryogenic plant cell and culturing the cell in a liquid medium to produce a cell suspension culture. The suspension culture is co-cultured, on a porous solid support, with a culture of *Agrobacterium tumefaciens* that harbors a vector comprising an exogenous gene and a selectable marker, the *Agrobacterium* being capable of effecting the stable transfer of the exogenous gene and selectable marker to the genome of the cell. A population of cells is thereby generated and those expressing the exogenous gene are selected and regenerated into transgenic plants.

In one aspect, using Green Florescent Protein (GFP) as a visual marker, it was discovered that cotton cell cultures could be transformed at surprisingly high efficiency (up to 200 kanamycin-resistant callus forming units per 200 mg cell mass) and could be regenerated into fertile plants at a much higher efficiency than previously reported.

In another aspect of the invention, previously unexplored tissues, such as cotton root or shoot tips dissected from mature seeds, are used for initiation and maintenance of suspension-cultured cells that maintain embryogenic competence.

Currently, two methods that have been disclosed relating to transformation of cotton somatic embryogenic materials via *Agrobacterium*-mediated T-DNA conjugation are the subject of U.S. Pat. No. 5,583,036 and U.S. Pat. No. 6,483,013. U.S. Pat. No. 5,583,036 refers to methods for the transformation of suspension cultures by co-cultivating in liquid medium cotton embryogenic callus with *Agrobacterium tumefaciens* bearing a Ti-plasmid that contained a gene of interest. U.S. Pat. No. 6,483,013 refers to a method for transformation of cotton embryogenic calli that were initiated and propagated on solid high auxin media and wherein the co-cultivation with *Agrobacterium tumefaciens* was performed on solid media Both methods employed somatic embryogenesis to regenerate fertile cotton plants. Here, as indicated, the invention provides methods for transformation of suspension cell cultures and their regeneration into fertile plants which represent improvements over these methods. In particular, the use of a co-culture technique carried out on a porous solid support, such as a membrane or filter, greatly enhances transformation efficiency in plants. Other aspects of the present invention include the use of various media compositions.

BRIEF DESCRIPTION OF THE FIGURES

(FIG. 3A) represents culture S16 cultured constantly in LM1; (FIG. 3B) shows culture S16 rotating in four different media (LM1, LM2, LM3, and LM4).

(FIG. 5A) No zeatin riboside in all subcultures; (FIG. 5B) 1 mg/l zeatin riboside added during the first subculture (only 2 sectors shown); (FIG. 5C) 1 mg/l zeatin riboside added during the first and second subcultures; (FIG. 5D) 1 mg/l zeatin riboside added during three subcultures.

(FIG. 7B); and depicts transformed, GFP+ cells 5 days after co-culture (FIG.7C)

(FIG. 14A) shows results from co-culture method described in U.S. Pat. No. 5,583,036. (FIG. 14B) shows results obtained according to the present inventive method.

(FIG. 15A) fresh pollen from transgenic plants derived from S16, (FIG. 15B), an aborted boll (from the same plant) with some fertilized ovules containing elongating fibers; (FIG. 15C); and an enlarging boll 10 days after pollinating the same plant with wildtype pollens (FIG. 15D).

DETAILED DESCRIPTION OF THE INVENTION

Figure 1:
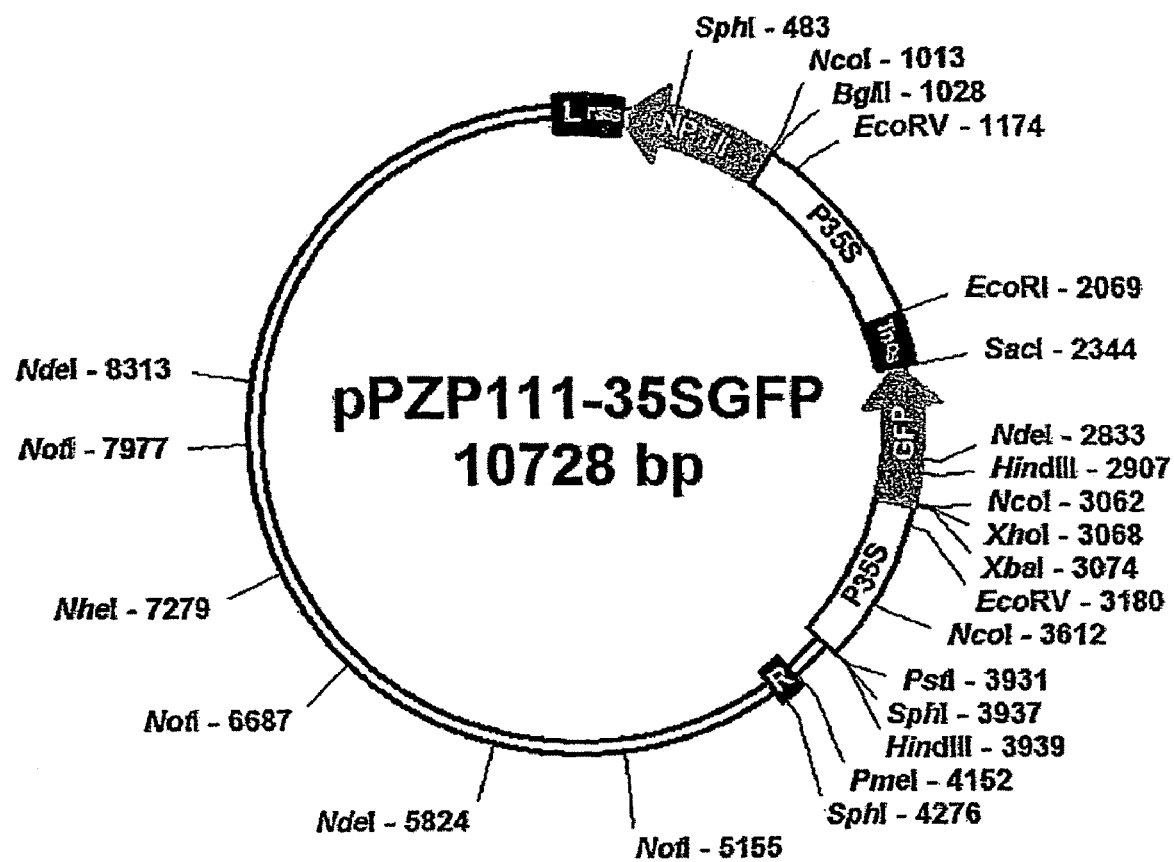
FIG. 1 shows gene organization of PZP111-35S:GFP. L and R represent the left and right borders, respectively. Plant selection marker gene (NPTII) is under control of CaMV 35S promoter and 35S terminator and GFP is under control of 35S promoter and Nos terminator.

The present invention relates generally to methods for production of transgenic plants, preferably cotton, maize, soybean, wheat, rice, and barley, and most preferably cotton, that express at least one gene of interest through integration of a copy of the gene in the nuclear genome. In particular, the invention provides a method for producing a transgenic plant, the method comprising providing a proembryogenic plant cell, and culturing the cell in a liquid medium to produce a cell suspension culture. On a porous solid support, the cell suspension culture is co-cultured with a culture of *Agrobacterium tumefaciens* that harbors a vector comprising an exogenous gene and a selectable marker, the *Agrobacterium* being capable of effecting the stable transfer of the exogenous gene and selectable marker to the genome of the cell. The co-culturing thereby generates a population of cells. A cell from the population that expresses the exogenous gene can be selected and regenerated into a transgenic plant. In an embodiment, the proembryogenic cell is derived from, obtained from, or is part of a callus. The porous solid support is preferably a membrane or a filter, and preferably comprises at least one of nylon, nitrocellulose, cellulose, or glass fibers. In an embodiment, the solid support is soaked in a liquid medium. In an alternate embodiment, the solid support is situated on an appropriate solid medium. The vector may be a plasmid, such as a Ti or Ri plasmid. The methods of the present invention represent an improvement over known methods of *Agrobacterium*-mediated transformation.

If desired, the resultant transgenic (transformed) plant, can be backcrossed with a germplasm of interest using methods well known in the art. The plant cell employed in the present methods can be from any plant, without limitation, but is preferably a cotton, maize, soybean, wheat, rice, or barley cell, and most preferably cotton. Preferred cotton species include *Gossypium hirsutum* and *Gossypium barbadense*. Other plants, including other dicotyledons are also suitable for transformation by the methods of the present invention.

In the present methods, the liquid medium can be a low auxin content medium (in a range, for example, from about 0 to about 0.1 mg/l NAA). Unless otherwise indicated, media used in the culturing steps of the methods described herein can be any media suitable and appropriate for the culture. Many such media are known and available in the art. Selection of cells is by chemical or genetic means, and can include the use of a reporter construct as a selectable marker. Such methods of selection are known in the art. In a preferred embodiment, the reporter construct constitutively expresses green fluorescent protein. A particularly preferred reporter construct is pPZP111-35S:GFP.

In an embodiment, the proembryogenic cell is obtained by sterilizing a plant seed, germinating the seed to generate plant tissue, obtaining an explant from the plant tissue, and inducing callus formation from the explant. The seed may be sterilized in a bleach solution, preferably a solution which comprises about 30% bleach. The seed can be germinated in MS medium, and such germination can take place over about 4-14 days. The explant is preferably a root or a shoot tip.

Methods of the present invention can further comprise inducing callus formation and initiating somatic embryogenesis in a solid medium, which can take place over a period of about one to about three months. Moreover, the methods can further comprise inducing differentiation of the callus to generate proembryogenic tissue, and such differentiation can preferably occur on a hormone-free, solid medium for a period of time sufficient to generate proembryogenic tissues, which are preferably suspended, maintained and propagated in a liquid medium or series of liquid media with low auxin content.

The suspension-cultured materials as described above are preferably sub-cultured regularly in a series of fresh media with differences in auxin content and nitrogen sources, and preferably at an interval of about 3 to about 30 days. The liquid media used as above preferably contains MS salt and B5 vitamins supplemented with low concentrations of auxin, preferably about 0-0.1 mg/l NAA and/or about 0-1 mg/l picloram. The alternative nitrogen sources, if present, are preferably amino acids, such as glutamine and/or asparagine, and preferably occur at concentrations of about 0.1-5 g/l. The solid or liquid media referred to above preferably has a pH value of about 5.8 to about 6.5, preferably about 6.0 to about 6.4. Suspension cultures can be maintained on a rotating platform with a temperature in the range of about 26° to about 32° C. and about a 16 hour lighting cycle.

The co-culturing described herein can further comprise growing the *Agrobacterium* strains of interest in a low phosphate liquid medium, preferably MinAB medium supplemented with an appropriate concentration of virulence inducing agents, to a preferred density of about 0.1-0.5 OD600 units, providing an *Agrobacterium* with a pre-induced virulence. The culture may be reconstituted in a liquid medium conducive to good growth of T-DNA recipient cells and enhanced expression of *Agrobacterium* virulence. Alternatively, *Agrobacterium* strains may be engineered to express constitutively active virA mutants by inserting the gene in either the *Agrobacterium* genome or Ti or Ri plasmid vectors within the *Agrobacterium*.

The suspension-cultured materials can be reconstituted in a liquid medium that is optimal for expression of *Agrobacterium* vir genes and mixed with *Agrobacterium* culture prepared as described, on a porous solid support, such as a membrane or filter. This mixture can be incubated under constant lighting for about 1-5 days. In an embodiment, the cells or calli are transferred to hormone-free medium supplemented with appropriate antibiotics to suppress growth of non-transformed plant cells and *Agrobacterium* cells. The porous solid support can be a membrane, or filter, as described, and can be laid upon a suitable solid medium or soaked in a suitable liquid medium, the media preferably containing either MS salt or MinAB salt supplemented with B5 vitamins and glucose and/or glycerol as a carbon source. These media preferably have a pH value between about 5.7 and about 6.5, preferably between about 5.7 and about 5.9. The co-cultivation preferably takes place at about 18-26° C., and under constant or continuous lighting.

The *Agrobacterium* culture can be a fresh preparation or one that is cryo-preserved, such as, for example, in the presence of about 0-20% DMSO; about 0-90% glycerol or about 0-5 M sorbitol or any combination thereof.

In an aspect, the invention also provides methods for regeneration of complete plants from pro-embryogenic suspension-cultured materials. Such methods include inducing reentry into embryogenic development and embryo proliferation by placing suspension-cultured materials, with or without prior co-culture with *Agrobacterium*, in a hormone-free MS-based medium with reinforced $KNO_3$, and subculturing regularly, such as for example, about every 3-4 weeks, in a medium with the same composition for a period sufficient to produce pre-globular to globular embryos. Further regular subculturing can be undertaken, again, for example, about every 3-4 weeks, in a solid, preferably MS-based medium supplemented with amino acids, preferably glutamine and asparagine at a concentration of about 0.1-5 g/l, and reinforced $KNO_3$ for about 4-12 weeks. Root and true leaf formation then can be induced in suitable media and resulting plantlets transferred into soil pots to produce flowering plants. The media included herein may be supplemented with appropriate antibiotics to inhibit growth of non-transformed cells and *Agrobacterium* cells when co-culture is employed. The subculturing can be performed in liquid medium, membrane-supported liquid medium, solid medium or other appropriate medium. These media preferably have a pH value of about 5.7 to about 6.5, more preferably about 6.0 to about 6.4. The cotton or other plant cells, somatic embryos and plantlets as referred to herein preferably are cultured at a temperature of about 25°-32° C. with about 16 hour lighting cycles. Co-cultured materials can be selected without prior washing.

The invention also provides a method, as an extension and complementation to the methods already described herein, for rescue of infertile plants and accelerated production of commercial varieties comprising manual pollination of the plants, including male sterile plants, with pollens derived from zygotic seeds of either the same variety or a specific germplasm of interest. Continued backcrossing in the following generations can be performed as needed or desired.

In preferred methods, the *Agrobacterium* comprises a virA gene mutant. The virA gene mutant can be incorporated into the genome of the *Agrobacterium* or incorporated into the vector.

In the described methods, the regeneration of cells into plants can be enhanced by addition of a cytokinin. For cotton, in particular, the cytokinin is preferably a zeatin or derivative thereof. Moreover, in an embodiment, the proembryogenic plant cell is initiated on a solid medium comprising a low concentration of 2,4-D and cytokinin. The proembryogenic cell may also be propagated in a hormone free liquid medium and/or a low auxin liquid medium.

Techniques for introducing exogenous genes into *Agrobacterium* such that they will be transferred stably to a plant or plant tissue exposed to the *Agrobacterium* are well-known in the art. It is advantageous to use a so-called "disarmed" strain of *Agrobacterium* or Ti plasmid, that is, a strain or plasmid wherein the genes responsible for the formation of the tumor characteristic of the crown gall disease caused by wild-type *Agrobacterium* are removed or deactivated. Numerous examples of disarmed *Agrobacterium* strains are found in the literature (e.g. pAL4404, pEHA101 and pEH 105 (Walkerpeach & Velten, 1994)). It is further advantageous to use a so-called binary vector system, such as that described in Schilperoort et al., 1990, 1995. A binary vector system allows for manipulation in *E. coli* of the plasmid carrying the exogenous gene to be introduced into the plant, making the process of vector construction much easier to carry out.

Similarly, vector construction, including the construction of chimeric genes comprising the exogenous gene that one desires to introduce into the plant, can be carried out using techniques well-known in the art. Chimeric genes should comprise promoters that have activity in the host in which expression is desired. For example, it may be advantageous to have a series of selectable markers for selection of transformed cells at various stages in the transformation process. A selectable marker (for example a gene conferring resistance to an antibiotic such as kanamycin, cefotaxime or streptomycin) linked to a promoter active in bacteria would permit selection of bacteria containing the marker (i.e., transformants). Another selectable marker linked to a plant-active promoter, such as the CaMV 35S promoter or a T-DNA promoter such as the NPT II NOS promoter, would allow selection of transformed plant cells. The exogenous gene that is desired to be introduced into the plant cell should comprise a plant-active promoter in functional relation to the coding sequence, so that the promoter drives expression of the gene in the transformed plant. Again, plant-active promoters, such as the CaMV 35S, the NPT II NOS promoter or any of a number of tissue-specific promoters, are well-known in the art and selection of an appropriate promoter is well within the ordinary skill in the art.

The present method can be used to produce transgenic plants expressing any number of exogenous genes, and is not limited by the choice of such a gene. The selection of the desired exogenous gene depends on the goal of the researcher, and numerous examples of desirable genes that could be used with the present invention are known in the art (e.g. the family of *Bacillus thuringiensis* toxin genes, herbicide resistance genes such as shikimate synthase genes that confer glyphosate resistance, U.S. Pat. No. 5,188,642, or a 2,4-D monooxygenase gene that confers resistance to 2,4-dichlorophenoxyacetic acid (2,4-D) (Bayley et al., 1992), male sterility genes such as the antisense genes of U.S. Pat. No. 5,741,684 (Fabijanski, et al.), or even the elaborate crop protection systems described in U.S. Pat. No. 5,723,765 (Oliver et al.)).

As evidenced herein, this invention provides, inter alia, methods utilizing different suspension initiation and maintenance procedures. As a non-limiting example, cotton root and shoot tips from mature seed were used as explants for callus induction in the presence of both cytokinin and a low concentration of 2,4-D. A somatic embryogenesis developmental pathway can be switched on upon transferring to hormone-free, high $KNO_3$-content solid medium. Suspension culture of selected callus can be initiated in a liquid medium with a similar composition supplemented with low concentration of auxin (0.01 mg/l NAA). Such cultures can be maintained at various stages of early embryogenic development depending on the time the callus was transferred to liquid medium. The cell cultures produced may undergo darkening with extended culture if the same medium was constantly used. However, an effective solution for this problem includes rotating the cultures in four variants of media. This allows the cultures to undergo a brief cell differentiation-proliferation cycle thanks to the embryo development-enhancing property of reduced nitrogen sources (Davidonis and Hamilton, 1983). The suspension cultures thus prepared have good synchrony in development and have a uniformly yellowish color. The embryogenic competence varies among different cell lines.

Further provided is a media composition for accelerated regeneration of somatic embryos from cell cultures via treatment with cytokinins that significantly improve early embryogenic development. Cytokinins have been found to play an important role in somatic embryogenesis (Xing et al., 1999; Sagare et al., 2000; Tokuji and Kuriyama, 2003). Their use in cotton regeneration, however, has never been reported. It was discovered that cytokinins, particularly zeatin riboside, significantly improved somatic embryo formation when used at the early stages of plant regeneration. Proper use of the hormone leads to shorter duration to reproduce complete plantlets due to increased conversion rate to globular stage embryos and accelerated development of leaves. Previously, regeneration of suspension cells was achieved by either culturing the cells in liquid medium or plating them out uniformly on solid media (Finer, 1988; European Pat. 0317512B1, U.S. Pat. No. 5,583,036). Both methods differ widely from the natural developing environment of zygotic embryos. Furthermore, as the materials need repeated subculturing, the plated calli are tedious to work with and slower growing transformants may be selected out during regeneration. This invention thus simplifies the handling process of suspension-cultured cells/calli by partially embedding in solid medium in sectors, which are easier for material transfer between subcultures and the cell clustering in such manner may prevent dehydration during culture in solid media.

Virulence of *Agrobacterium* is known to be influenced by environmental pH and temperature. Optimal virulence occurs at around pH5.7 below 25° C. (Rogowsky, et al., 1987; Fullner and Nester, 1996). These factors have been taken into account to develop medium different from that which has been used for high efficiency transformation of filamentous fungi (Bundock et al., 1995; de Groot et al., 1998), to accommodate healthy growth of plant cells, particularly cotton. Co-culture is performed at around 24° C. with pre-induced cultures. Alternatively, *Agrobacterium* strains may be engineered to express virA mutants (McLean et al., 1994).

In light of the preceding description, one of ordinary skill in the art can practice the invention to its fullest extent. The following examples, therefore, are merely illustrative and should not be construed to limit in any way the invention as set forth in the claims which follow.

A reporter construct, pPZP111-35S:GFP (Xu et al., unpublished data) that constitutively expresses the Green Fluorescent Protein (GFP) (FIG. 1) was used to illustrate the technical processes and monitor the effectiveness of the procedures. As indicated, other suitable markers may also be used.

EXAMPLE 1

Generation of Cotton Suspension Cell Cultures from Explants

Cotton seeds are sterilized by soaking in 30% bleach solution for 45-90 minutes. After thorough rinsing in water, seeds are incubated in water at 28° C. for 1 day and further incubated on SGM medium at 28° C. with 16 hours lighting for 4-14 days. Roots are cut into short (3-5 mm) segments and allowed to develop calli on SM1 medium for approximately one month. Alternatively, embryogenic shoot tips may be dissected out from the seeds and used for callus induction. The calli are separated from the explants and further incubated on SM1 medium for approximately one month. To induce somatic embryogenesis, the calli are transferred to SM2 medium, subcultured every 3-4 weeks on fresh medium until loosely structured yellowish or reddish calli are obtained. Up to 200 mg of the isolated callus are placed in 50 ml LM1 medium in a suitable container, for example, a 250 ml conical flask or cylinder tissue culture container, and incubated at 28° C. on a shaking platform (120 RPM) with 16 hours lighting cycles. The cells/callus tissues are subcultured, typically every 7-14 days by transferring 15 ml of the culture (approximately 2 ml cell mass in a stabilized culture) to 35 ml fresh medium in a new container. Four variants of liquid media (LM1, LM2, LM3 and LM4) are used cyclically.

EXAMPLE 2

Introduction of a Gene of Interest into Cotton Cells

A gene of interest is delivered into cotton cells via *Agrobacterium*-mediated T-DNA conjugation by co-cultivation of freshly subcultured cotton suspension culture with a culture of *Agrobacterium* that harbors the gene of interest and a dominant selection marker in an appropriate Ti or Ri plasmid vector. The mixtures are co-spotted on a sheet of porous membrane or filter paper laid atop a SIM1 or SIM2 plate for a time sufficient to produce a desired number of transformed cotton cells. Alternatively, 3-4 sheets of filter paper that have been soaked with a liquid medium may be used in place of the solid medium. For best results, pre-induced *Agrobacterium* culture prepared as described for transformation of filamentous fungi are used although common bacterium cultures may be used (de Groot et al., 1998).

EXAMPLE 3

Regeneration into Transgenic Cotton Plants from Transformed Cells

Figure 7:
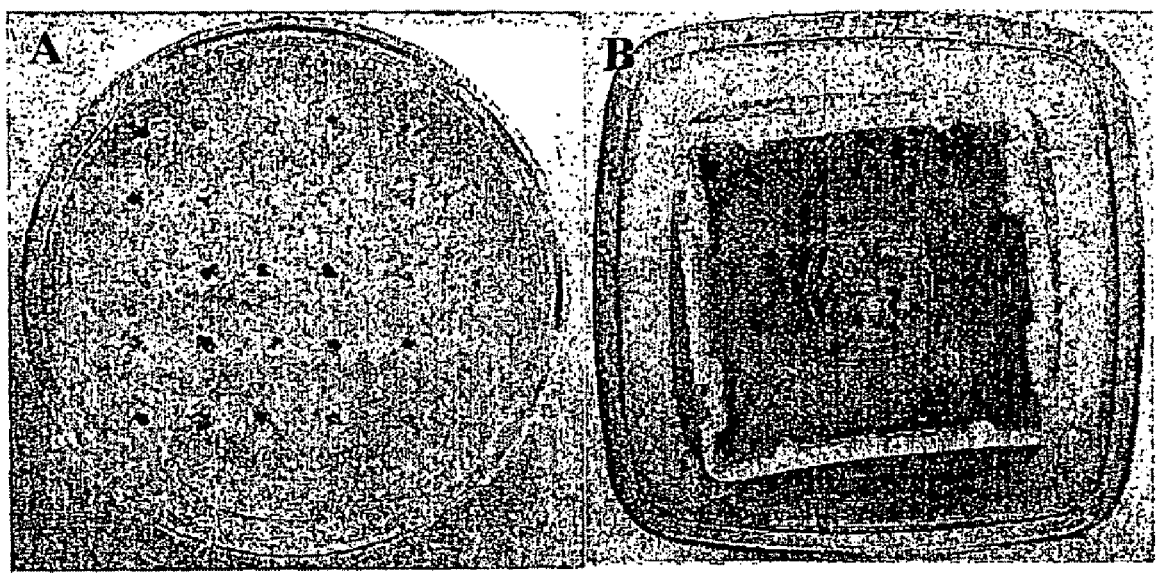
FIGS. 7A-7C shows selection on solid R1 medium in sectors; 7A; and selection on a culture raft in liquid medium.

After co-cultivation, the cells are transferred to R1 medium supplemented with appropriate antibiotics for suppression of non-transformed cotton cells and the *Agrobacterium* cells that remain attached. Selection of transformed plant cells may also be achieved by visual markers. The co-cultured cotton cells need no wash and can be transferred to selective solid medium as callus "sectors" (normally 100-150 per co-culture). Alternatively, each co-culture may be transferred as a whole onto a culture raft in the same medium lacking phytagel (FIG. 7). Culture in liquid medium is normally limited to the initial 3-4 weeks. After that, it preferably is transferred to solid R1 medium. A further 3-4 weeks in medium R1 is normally required so that multiple embryos can be obtained. Further culture in R1 medium is possible if the undifferentiated embryos were not seen. Subsequently, the antibiotic resistant globular or later stage embryos are cultured on R2 medium for 3-4 weeks and this is repeated one more time. Antibiotics may be omitted from the $2^{nd}$ culture on R2 medium. Fully developed embryos (no root, with cotyledons) or green embryo-like tissues with no obvious cotyledons are transferred to R3 medium and full plantlets are transferred to R4 medium. In about 3-4 weeks, plantlets are planted in soil pots.

EXAMPLE 4

Preparation of Suspension Cell Cultures

Figure 2:
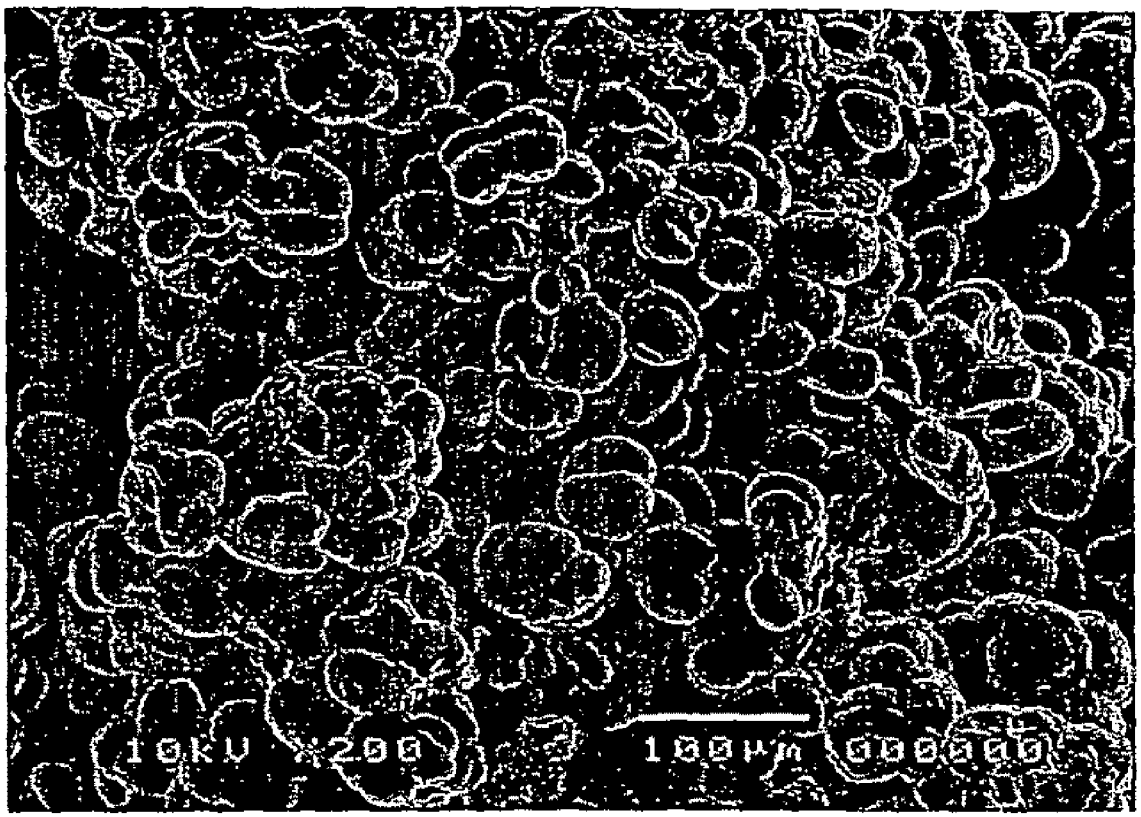
FIG. 2 shows the structure of pro-embryogenic calli (S4) propagated in suspension cultures.
Figure 3:
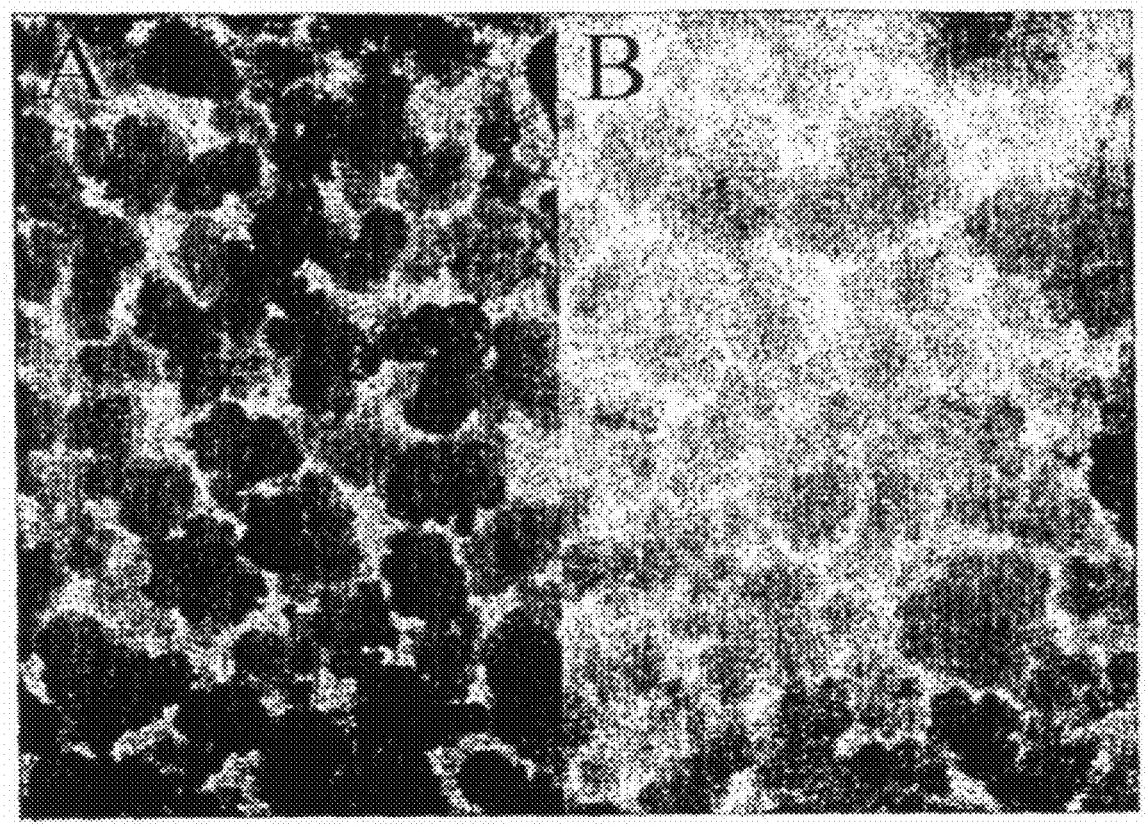
FIGS. 3A-3B shows darkening of suspension cultures and solutions.

Cotton seeds (Coker 312) were sterilized by soaking in 30% bleach (Clorox) solution for 45 minutes and, after two washes in water, incubated in water at 28E C for one day. The seeds were further incubated on SGM medium at 28E C with 16 hours lighting cycles for 4 days. White-colored roots were cut into short (3-5 mm) segments and allowed to develop calli on SM1 medium for approximately one month. The calli were separated from the explants and incubated on the same medium for approximately one more month. The calli were transferred to SM2 medium, subcultured approximately every 3-4 weeks on fresh medium until loosely structured calli were obtained. Approximately 200 mg of the isolated callus were placed in 50 ml LM1 medium in a 250 ml conical flask and incubated at 28° C. on a shaking platform (120 RPM) with 16 hour lighting cycles. The suspension cultures were subcultured every 7-14 days by transferring a 15 ml of aliquot (approximately 2 ml cell/calli mass in a stabilized culture) to 35 ml fresh medium in a new container. Among 5 calli selected, three stabilized as vigorous growing yellowish cultures consisting of calli of various sizes when the subculture was performed cyclically in four different media (LM1, LM2, LM3, and LM4). The calli showed no or limited embryogenic structure when examined under a scanning electron microscope (FIG. 2). Severe browning or darkening could occur if a single medium was constantly used (FIG. 3). Cultures S4 and S5 both successfully developed into somatic embryos when they were transferred to solid medium R1.

EXAMPLE 5

Preparation of Cell Suspension Cultures

Cotton seeds were sterilized by soaking in 30% bleach (Clorox) solution for 45 minutes and, after two washes in water, incubated in water at 28E C for 24 hours. The seeds were further incubated on SGM medium at 28E C with 16 hour lighting cycles for 4 days. White-colored roots were cut into short (3-5 mm) segments and allowed to develop calli on SM1 medium for one month. The calli were separated from the explants and cultured on the same medium for approximately one more month. The calli were transferred to SM2 medium and subcultured every 3-4 weeks on fresh medium until loosely structured calli were obtained. Up to 200 mg of the isolated callus were placed in 50 ml LM1 medium in a 250 ml conical flask and incubated at 28° C. on a shaking platform (120 RPM) with 16 hour lighting cycles. The suspension cultures were subcultured every 7 days by transferring a 15 ml aliquot (approximately 2 ml cell/calli mass when the cultures were stabilized) to 35 ml fresh medium in a new container. Among 3 calli selected, two stabilized as vigorous growing yellowish calli when subculture was performed cyclically in four different media (LM1, LM2, LM3, and LM4). Cultures S15 and S16 both successfully developed into somatic embryos when they were transferred to solid medium R1.

EXAMPLE 6

Preparation of Cell Suspension Cultures

Cotton seeds were sterilized by soaking in 30% bleach (Clorox) solution for 45 minutes and incubated in water at 28E C for 24 hours after rinsing twice with water. The seeds were further incubated on SGM medium at 28E C with 16 hours lighting cycles for 4 days. White-colored roots were cut into short (3-5 mm) segments and allowed to develop calli on SM1 medium for approximately one month. In addition, embryogenic shoot tips were dissected from the sterilized seeds and used for callus induction as with the root explants. A month later, yellowish calli at the tips of both of kinds of explants were dissected out and incubated in the same medium for one more month. The calli were transferred to SM2 medium, subcultured every 3-4 weeks on fresh medium until loosely structured calli were obtained. Approximately 200 mg of the isolated callus were placed in 50 ml LM1 medium in a 250 ml conical flask and incubated at 28° C. on a shaking platform (120 RPM) with 16 hours lighting cycles. The suspension cultures were subcultured every 7 days by transferring a 15 ml aliquot (approximately 2 ml cell/calli mass when cultures were stabilized) to 35 ml fresh medium in a new container. All 7 selected calli stabilized as vigorously growing yellowish calli.

EXAMPLE 7

Effects of Cytokinins on Early Embryogenic Development

Figure 4:
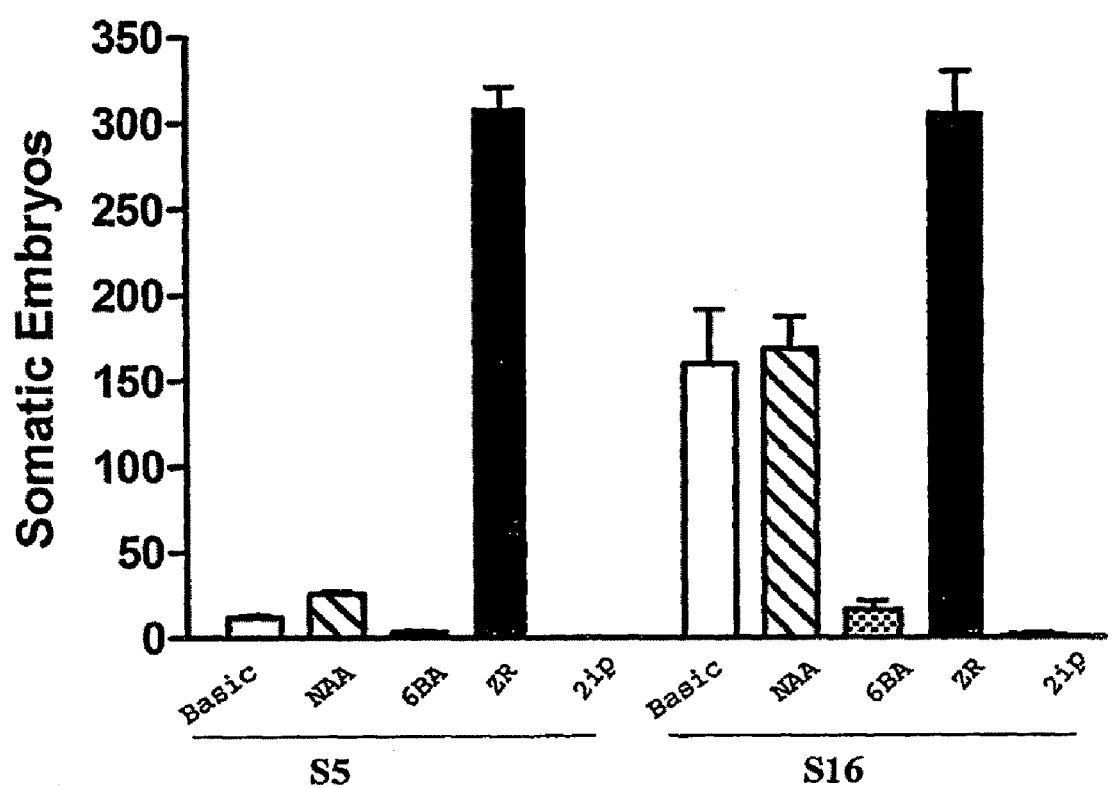
FIG. 4 shows the effects of cytokinins on somatic embryo yield. Approximately 0.1 mg calli mass was plated on either MS medium (basic), or MS supplemented with 0.01 mg/l NAA (NAA), 1 mg/l 6BA (BA), 1 mg/l 2IP or 1 mg/l zeatin riboside (ZR). S5 and S16 are two suspension cultures. The number of somatic embryos were scored after one month. Results shown represent the average of three replica plate sets.

Approximately 0.1 g of the suspension-cultured calli mass was plated out in medium R1 supplemented with 0.01 mg/l NAA supplemented either 1 mg/l 6BA, 2IP or zeatin riboside. The number of globular or later stage embryos was scored after 5 weeks incubation. In both cultures tested (S5 and S16), zeatin riboside treatment led to significant increases in the yield of embryos (FIG. 4).

EXAMPLE 8

Effects of Cytokinins on Early Embryogenic Development

Figure 5:
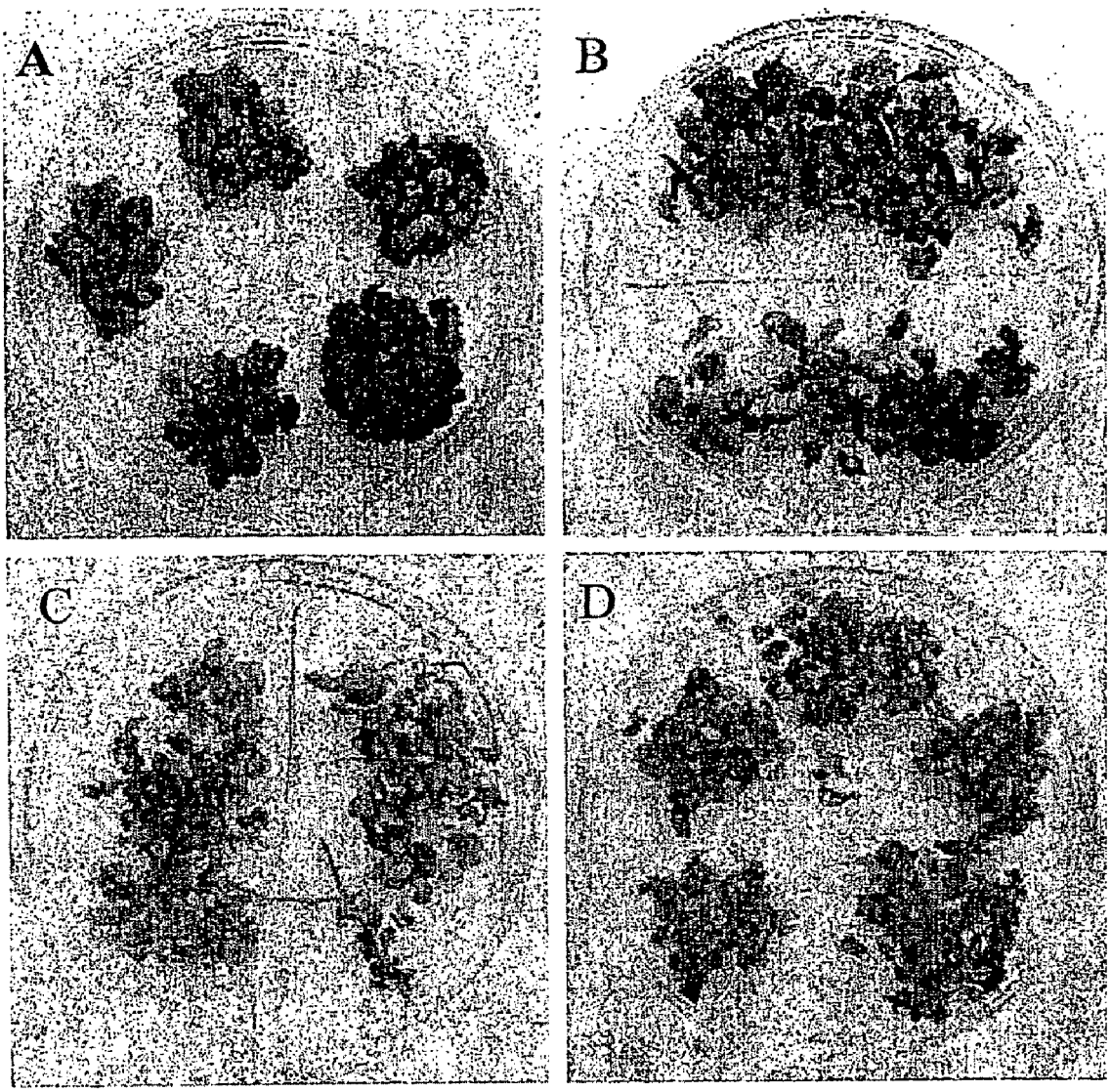
FIGS. 5A-5D depict the effect of zeatin riboside on somatic embryo production with respect to S5 suspension cultures after two subcultures in R1 medium and one subculture in R2 medium. The panels are as follows.

Pro--embryogenic calli were placed in R1 medium with or without 1 mg/l zeatin riboside. The calli were cultured on the zeatin riboside-containing R1 medium for 1-3 months. A significant increase in the number and sizes of embryos was observed in plates treated with zeatin riboside and the effect became more dramatic with continued exposure to zeatin riboside (FIG. 5).

EXAMPLE 9

Transformation of Suspension Culture with Induced *Agrobacterium* Culture

Binary T-DNA vector, pPZP111-35S:GFP, was introduced into *Agrobacterium tumefaciens* strain AGL1 by electroporation. A saturated culture of the strain was diluted 5-fold with IM medium and further incubated at 28° C. for 6 hours until it reached approximately 0.3 $OD_{600}$ unit. Approximately 0.5 ml of suspension cultures S5, and S5 that were cultured either in LM1, LM2, LM3 and LM4 was mixed with 0.2 ml *Agrobacterium* culture and co-spotted on a Hybond N membrane (Amersham Pharmacia) that was laid atop R1 medium supplemented with 100 μM acetosyringone. After 3 days of co-culture at 24° C. with constant lighting, the calli on nylon membranes were rinsed with a suspension medium (e.g., LM1 supplemented with 100 mg/l kanamycin and 450 mg/l Cefotaxime). The whole membrane was transferred to R1 or R2 medium supplemented with 100 mg/l kanamycin and 300 mg/l Cefotaxime and cultured at 28° C. with 16 hour lighting cycles. GFP positive calli were seen after one month. The remaining *Agrobacterium* culture was dispensed into 0.5 ml aliquots and equal volume of 14% DMSO was added. The bacterium stock was stored frozen at +80° C. until use.

EXAMPLE 10

Transformation of Suspension Cultures

Figure 6:
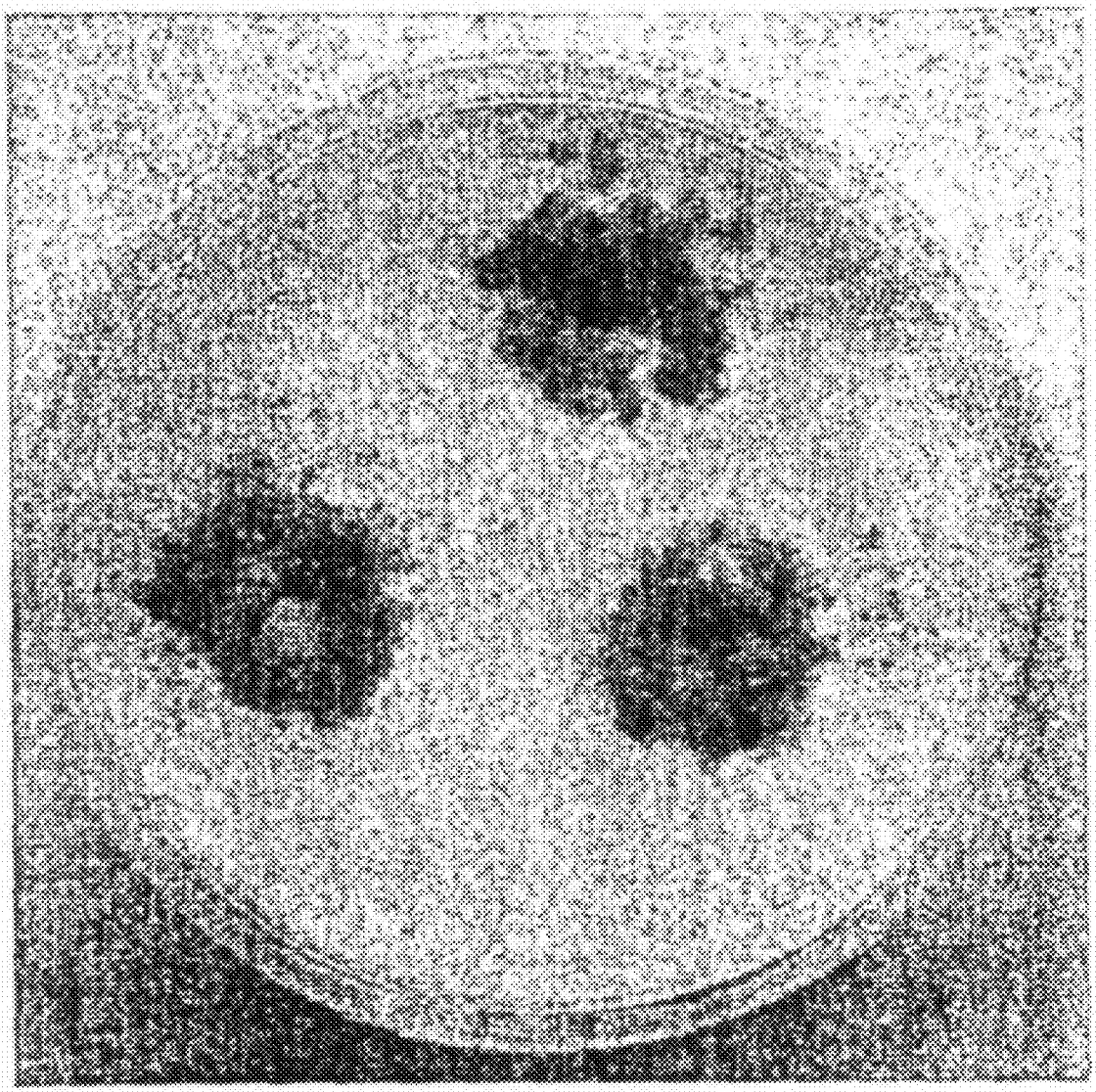
FIG. 6 shows co-culture of T-DNA recipient cells and donor cells on a nylon membrane (Hybond-N).
Figure 7C:
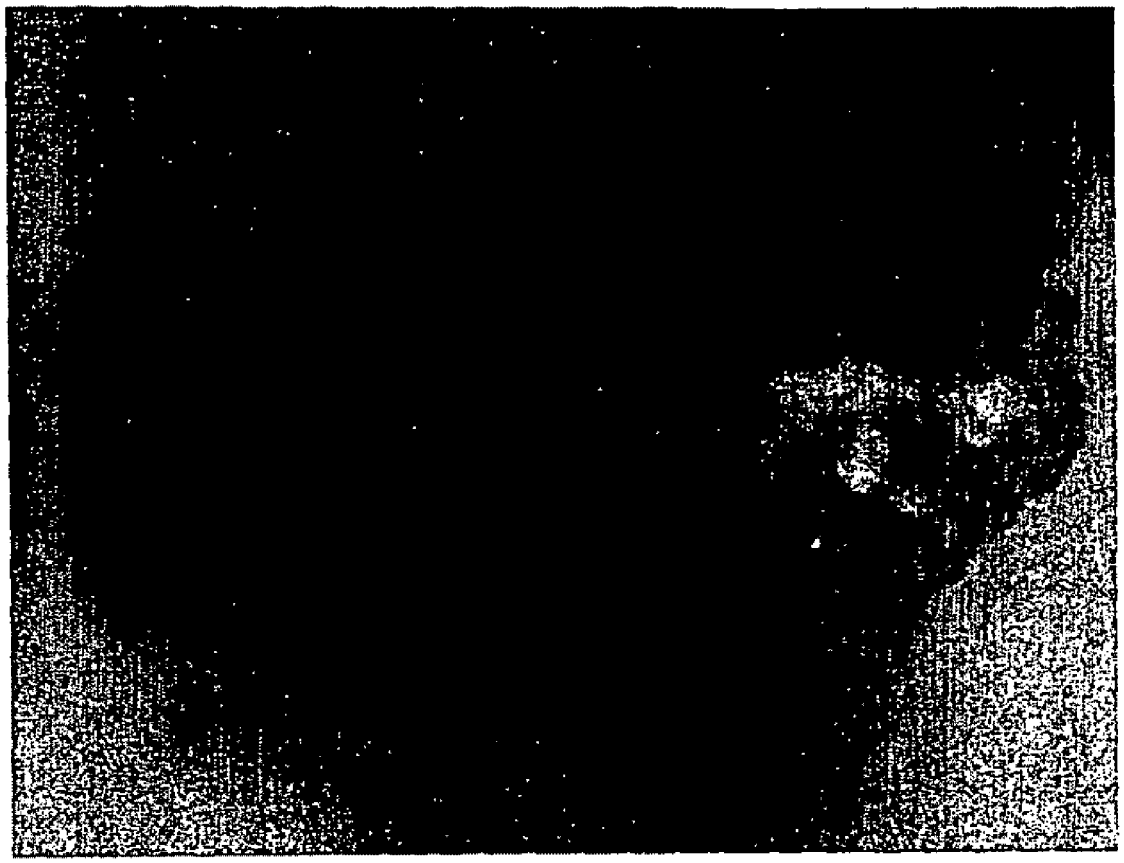
Figure 8:
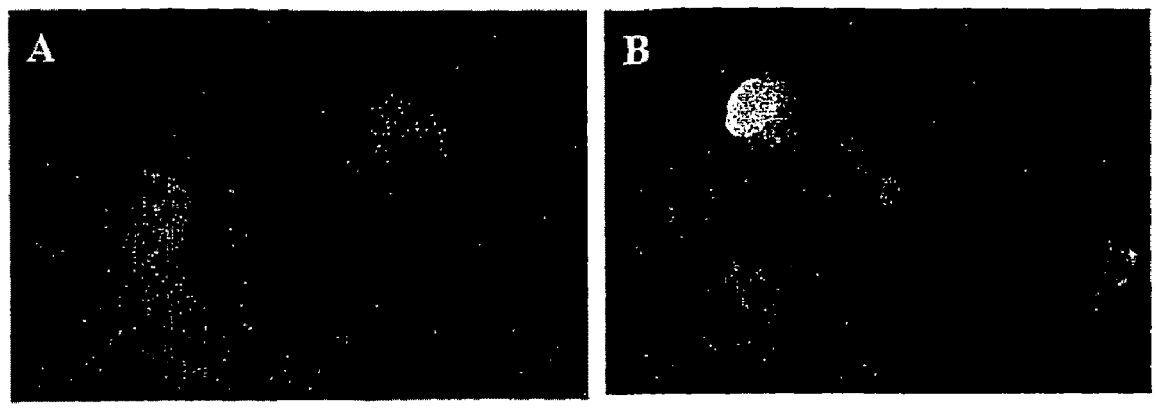
FIGS. 8A-8B depict transformed GFP+embryos (FIG. 8A) and embryonic tissues (FIG. 8B) one month after culture on selective medium R1.
Figure 9:
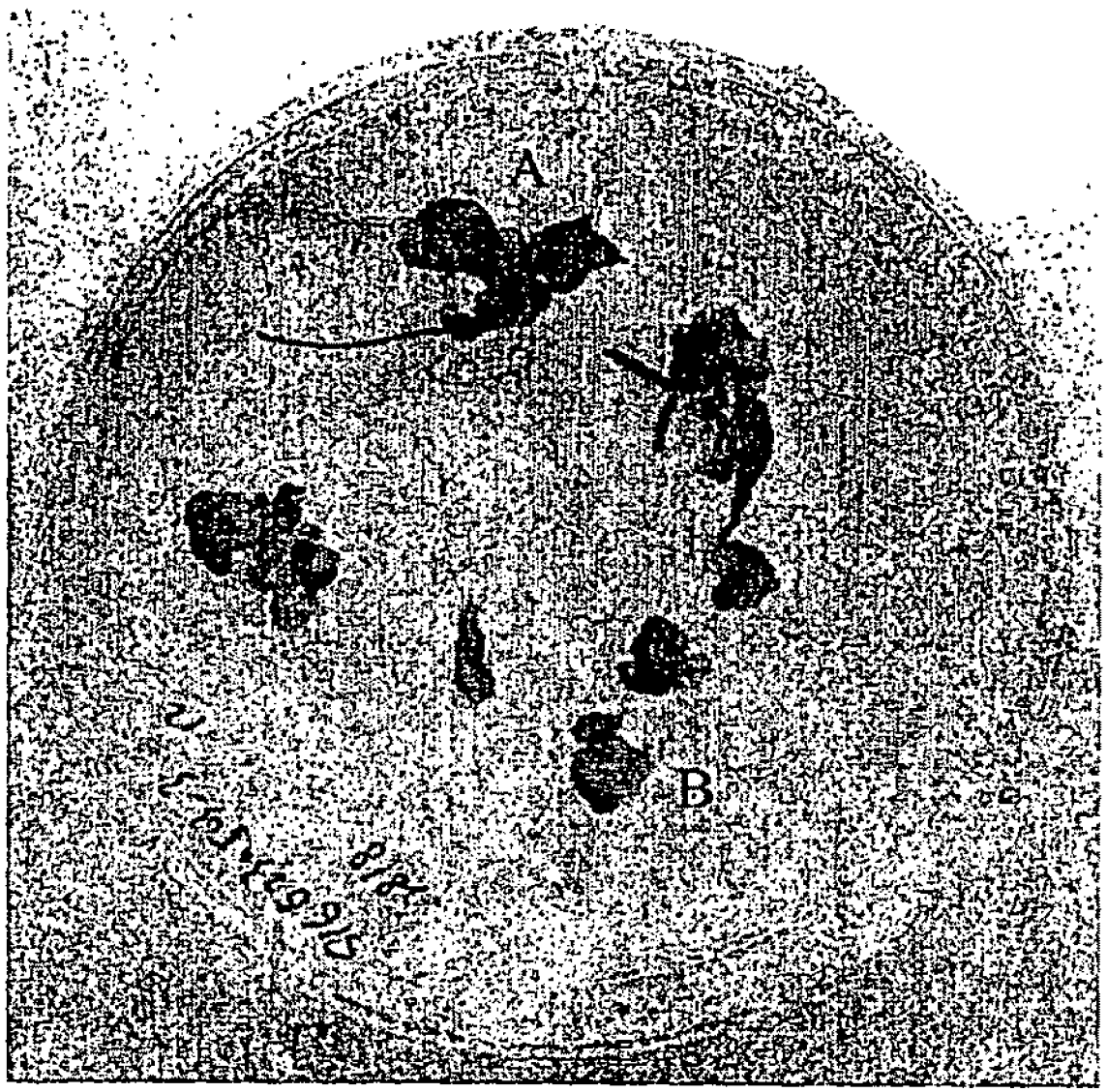
FIG. 9 shows germinated embryos (A) and embryo-like tissues (B) 4 months after co-culture.
Figure 10:
FIG. 10 shows plantlets with multiple shoots derived from embryo-like tissue.

Just before use, a tube of the frozen AGL1 culture was thawed and the bacterial cells were collected by centrifugation. The pellets were resuspended in 0.5 ml C1 medium (pH 5.7) mixed with 0.5 ml (approximately 0.2 g cell mass) and co-spotted on a Hybond-N membrane (Amersham Pharmacia) or Whatman 4 filter paper atop CP1 medium (pH5.7). Multiple independent co-cultures (3-4) could be performed on a single membrane (FIG. 6). After co-culture, the cells/calli were transferred (without washing) to medium R1 supplemented with 100 mg/l kanamycin and 200 mg/l Cefotaxime and cultured at 28° C. with 16 hours lighting cycles. Each co-culture was divided into up to 160 sectors, each representing a single large calli or a small clump of micro-calli (FIG. 7A). Alternatively, the whole co-culture was transferred to a culture raft on LM1 supplemented with 100 mg/l kanamycin and 200 mg/l Cefotaxime (FIG. 7B). Distinct foci of green fluorescence were visible from the 5$^{th}$ day on selective medium (FIG. 7C). After 4 weeks in R1 medium, the kanamycin resistant sectors were transferred individually to solid R1 medium supplemented with the same antibiotics. In the meantime, the liquid-cultured calli were transferred to solid selective medium R1. Each sector was examined under fluorescent microscope for green fluorescence at various time points after co-culture. GFP positive somatic embryos started to appear in about one month (FIG. 8). By 3 months after co-culture, up to 38 sectors were found to contain embryos positive for green fluorescence in a single co-culture. Sectors positive for GFP but not yet producing somatic embryos are several folds higher. Both types of co-culture support gave satisfactory results, which are summarized in Table 1.

nylon membranes atop CP1 medium (pH5.7). After co-culture, the calli were transferred (without washing) to medium R1 supplemented with 100 mg/l kanamycin and 200 mg/l Cefotaxime and incubated at 28° C. with 16 hour lighting cycles. Each co-culture was divided into up to 160 sectors, each representing a single large calli or a small clump of micro-calli. Alternatively, the whole co-culture was transferred to a culture raft on LM1 supplemented with 100 mg/l kanamycin and 200 mg/l cefotaxime. After two months in selective R1 medium, the kanamycin resistant sectors were transferred to fresh R1 plates supplemented with 1 mg/l zeatin riboside with the same antibiotics and continued culturing for 4.5 weeks. Kanamycin resistant calli were transferred to R2 medium supplemented with 50 mg/l kanamycin and 200 mg/l cefotaxime. This is repeated two more times in antibiotics-free R2 medium and large, vigorously growing embryos or green calli, which may appear in the first R2 culture, were selected and transferred to R3 medium. Embryos may germinate and develop roots and true leaves (FIG. 9A). Interestingly, the zeatin treatment allowed many cotyledon-less abnormal embryo and even green tissues, such as those shown in FIG. 9B, to develop into shoots. Often, multiple shoots were developed (FIG. 10). Plantlets that had 1. Effects of Different Supports and Regeneration Media

|  | Support type | 1st medium | Total Sector | GFP+ | GFP+ | GFP+ Date | embryos+ | GFP+ | embryo+ |
| --- | --- | --- | --- | --- | --- | --- | --- | --- | --- |
|  |  |  | 28 May 2003 | 28 May 2003 | 24 Jun. 2003 | 30 Jul. 2003 | 30 Jul. 2003 | 30 Aug. 2003 | 30 Aug. 2003 |
| S4G020503-11 | HybondN | R1-plate[1] | 120 | 2 | 8 | 14 | 0 | 11 | 1 |
| S4G020503-12 | HybondN | R1-plate | 160 | 32 | 69 | 61 | 6 | 52 | 20 |
| S4G020503-13 | Whatman 4 | R1-plate | 180 | 23 | 63 | 72 | 13 | 69 | 38 |
| S4G020503-14 | Whatman 4 | R1-plate | 100 | 7 | 19 | 28 | 4 | 18 | 10 |
| S4G020503-1 | HybondN | R1-raft[2] | 100 | 6 | 39 | 41 | 7 | 36 | 11 |
| S4G020503-2 | HybondN | R1-raft | 140 | 21 | 114 | 118 | 14 | 94 | 31 |
| S4G020503-3 | Whatman 4 | R1-raft | 140 | 9 | 39 | 40 | 7 | 33 | 14 |
| S4G020503-4 | Whatman 4 | R1-raft | 135 | 5 | 8 | 7 | 0 | 8 | 1 |
| S5G020503-11 | HybondN | R1-plate | 100 | 16 | 72 | 76 | 23 | 61 | 26 |
| S5G020503-12 | HybonR1N | R1-plate | 180 | 31 | 152 | 143 | 29 | 115 | 37 |
| S5G020503-13 | Whatman 4 | R1-plate | 155 | 27 | 108 | 105 | 12 | 88 | 27 |
| S5G020503-14 | Whatman 4 | R1-plate | 160 | 47 | 135 | 108 | 16 | 97 | 34 |
| S5G020503-4 | Whatman 4 | R1-raft | 160 | 60 | 135 | 102 | 21 | 90 | 15 |

Note:
[1]Solid medium R1 with 100 mg/l kanamycin, 200 mg/l Cefotaxime.
[2]Liquid medium R1 with 100 mg/l kanamycin, 200 mg/l Cefotaxime. Cultured in Gibco BRL liquid culture system.

EXAMPLE 11

Transformation of Suspension Cultures with a pPZP111-35S:GFP Construct

Figure 11:
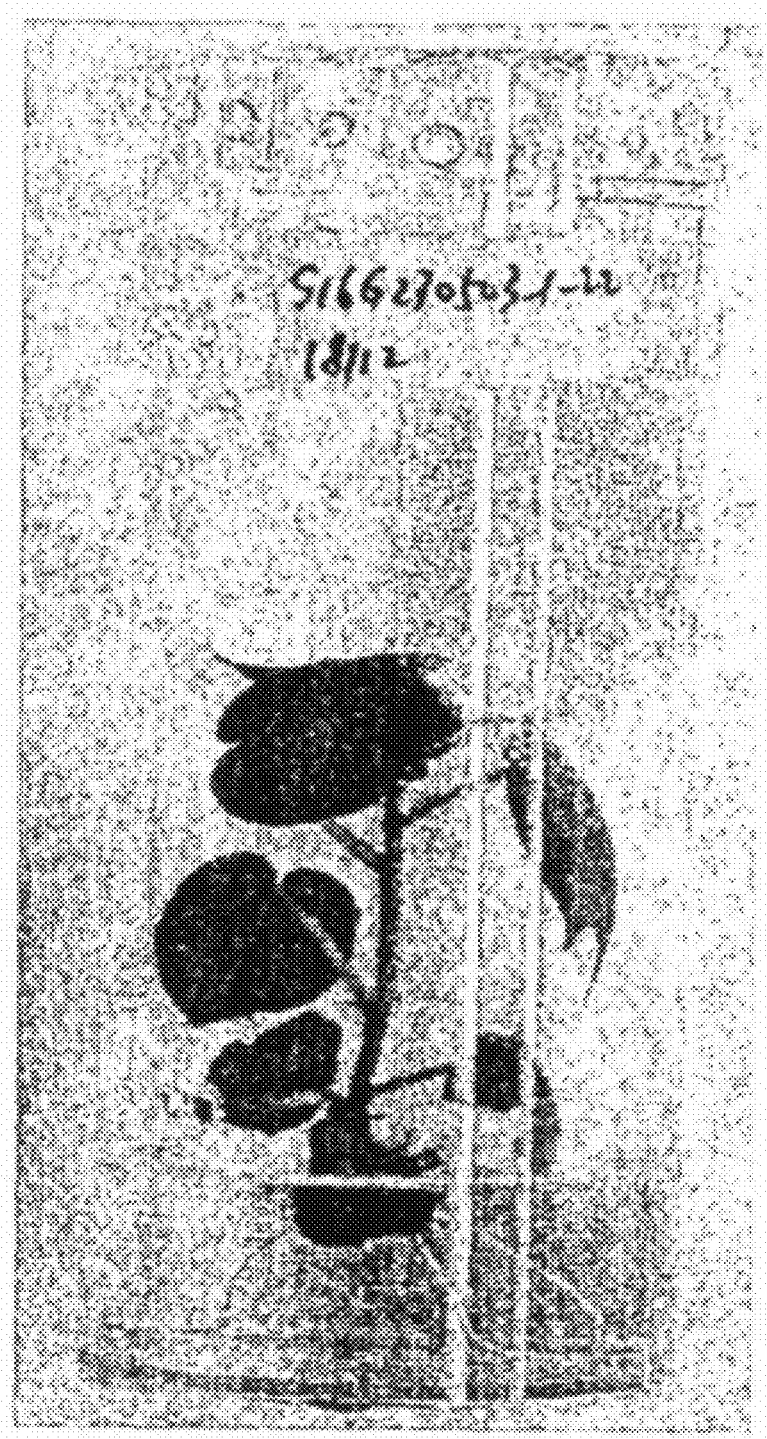
FIG. 11 shows potting ready plantlets derived from a germinated somatic embryo.
Figure 12:
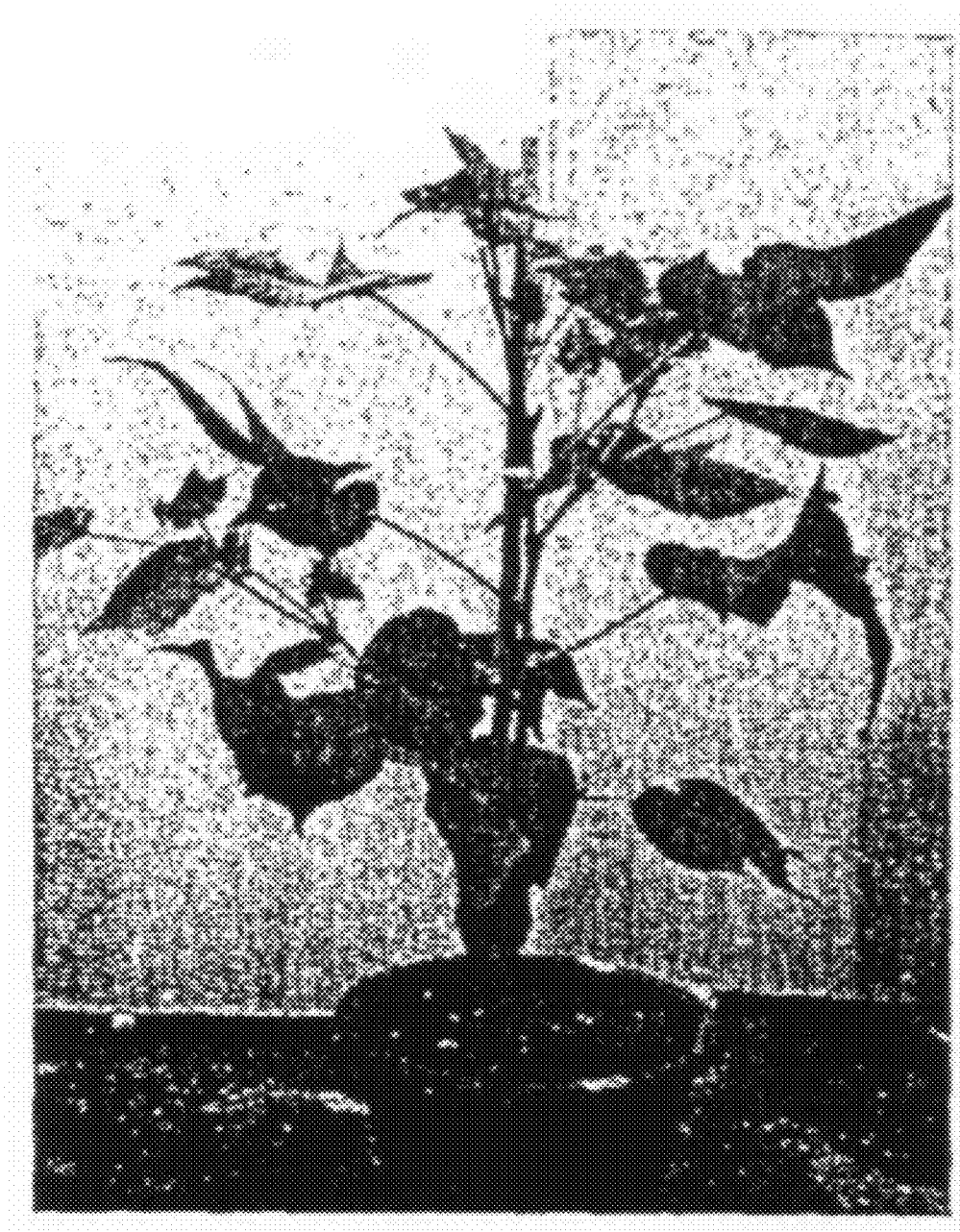
FIG. 12 shows healthy flowering plants 7-8 months after co-culture.
Figure 13:
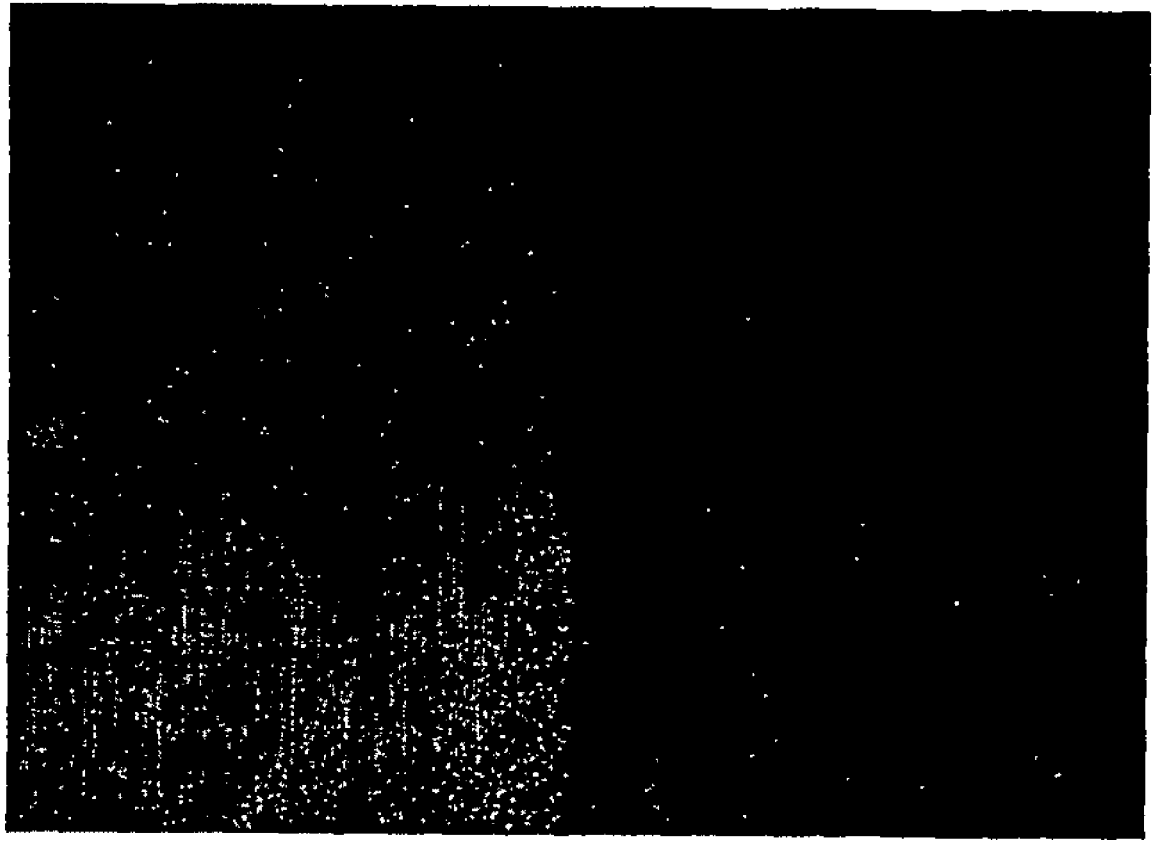
FIG. 13 shows GFP+leaves from a transgenic adult leaf (left panel) and background fluorescence from a non-transformed adult plant.

A tube of the frozen AGL culture harboring pPZP111-35S: GFP was thawed and the bacterial cells were collected by centrifugation. The bacterial pellets were resuspended in C1 (pH5.7). Suspension cultures (S4, S5 and S16) were washed in the C1 medium. Approximately 0.5 ml cultures were mixed with 0.4 ml Agrobacterium suspension and co-cultured on developed true leaves were plentiful in 3-4 weeks and were cultured in R4 medium for further leaf and root development (FIG. 11). Plantlets with 6-8 leaves were potted in soil and by about 7-8 months after co-culture, the plants started to flower (FIG. 12). Approximately 77% of the adult plants were positive for GFP fluorescence (FIG. 13). Up to 26 healthy plants could be produced from a single co-culture. Of the 18 putative transformants analyzed by Southern blotting analysis, 17 were positive for the GFP transgene (95%) and 7 contained a single transgene (39%). The detailed results of the transformation were shown in Table 2.

TABLE 2

Summary of Transformation Done on 23 May 2003

| | Date | | | | | | | | | GFP+ |
|---|---|---|---|---|---|---|---|---|---|---|
| | 26 May 2003 Sectors | 21 Jun. 2003 Sectors | 24 Jul. 2003 KanR No. | GFP+ | 27 Aug. 2003 KanR No. Medium | GFP+ 1st Plantlet | | Healthy Family | First Flower | |
| | R1-K100C | R1-K100C | R1-ZK50C | | R1-K50C | R4 | | | Soil | % plants |
| S4G230503-2 | 120 | 120 | 41 | 12 | 11 | 7 | | | | |
| S4G230503-3 | 120 | 120 | 16 | 7 | 6 | 3 | | | | |
| S5G230503-2 | 120 | 120 | 94 | 23 | 60 | 43 | 13 Oct. 2003 | | | |
| S5G230503-3 | 120 | 120 | 68 | 27 | 66 | 44 | 15 Sep. 2003 | | | |
| S16G230503-2 | 120 | 120 | 88 | 59 | 72 | 62 | 22 Sep. 2003 | 19 | 26 Dec. 2003 | 89% |
| S16G230503-3 | 160 | 160 | 138 | 87 | 113 | 97 | 22 Sep. 2003 | 26 | 26 Dec. 2003 | 69% |
| S16G230503-4 | 160 | 160 | 132 | 89 | 117 | 105 | 22 Sep. 2003 | 26 | 02 Jan. 2004 | 72% |

Note:
All the figures represent sector numbers. Healthy family indicates sectors that have developed at least one plant with normal flower plant.
R1-K100C: R1 medium with 100 mg/l kanamycin, 200 mg/l cefotaxime
R1-K50C: R1 medium with 50 mg/l kanamycin, 200 mg/l cefotaxime
R1-ZK50C: R1-K50C medium with 1 mg/ml zeatin riboside

EXAMPLE 12

Effects of pH in Co-culture Media

Frozen *Agrobacterium* stocks prepared previously were collected by centrifugation and suspended in C1 with pH adjusted to 5.2, 5.7, 5.9 and 6.2. Approximately 0.2 mg suspension cell mass was mixed with 0.4 ml *Agrobacterium* suspension and co-cultured on nylon membranes atop the corresponding solid medium (CP1, pH 5.2-6.2). Three sets of co-cultures were performed under each condition. The number of sectors showing GFP fluorescence was scored after 2 months culture on selective R1 medium. Significantly better results were obtained with medium pH higher than 5.2. On average, 71%, 81% and 83% of callus sectors were positive for GFP fluorescence in C1-pH5.2, C1-pH 5.7 and C1-pH6.2, respectively.

EXAMPLE 13

Comparison of Co-culture Methods

Figure 14:
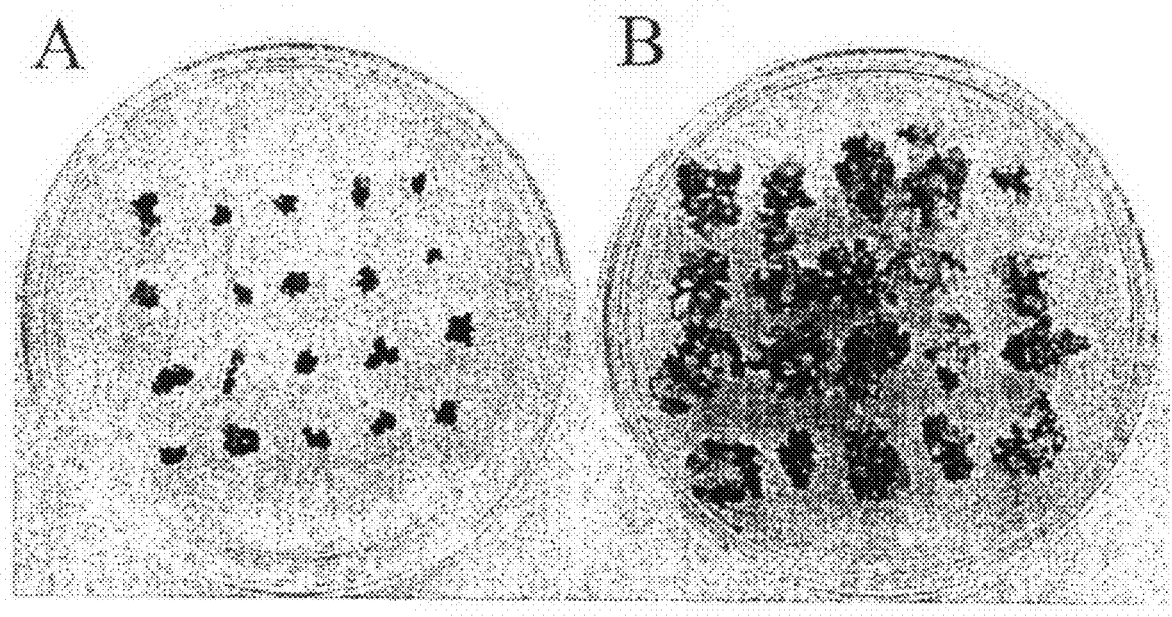
FIGS. 14A-14B show callus sectors cultured in selective R1 medium for one month.

To determine factors that contributed to the high transformation efficiency obtained with the present methods, we performed transformation of our suspension cell cultures using the method essentially as disclosed previously (U.S. Pat. No. 5,583,036). The T-DNA donor preparation, AGL1 strain harboring pPZP111-35S:GFP, was made in LB medium. The bacterium cells were collected by centrifugation and resuspended in MS medium supplemented with 1 mg/l NAA to 0.5 OD600 unit. Approximately 0.2 g suspension cultures (S5 and S16) was mixed with 2 ml fresh *Agrobacterium* culture in a conical flask which was left at 28° C. for two hours for the *Agrobacterium* cells to attach to the suspension cells. After removing the liquid medium, 10 ml MS medium supplemented with 1 mg/l NAA was added to the flask. The cells were cultured on a shaking platform (100 rpm) for 18 hours. The suspension cells were then washed (twice) with MS medium and placed on selective R1 medium in sectors. In a parallel experiment, the same *Agrobacterium* strain was prepared freshly with no freezing as described in Example 9. Cultures S5 and S16 were co-cultured as described in Example 10. After 30 days of culture on selective R1 medium, the number of somatic embryos was scored. While about 64% (S5) and 83% (S16) of the calli sector were positive for GFP fluorescence when co-culture was performed using our method, the rates dropped to only 1% (S5) and 13% (S16) respectively when co-culture was performed in liquid medium in an agitating conical flask (FIG. 14). It is also clear that the kanamycin resistant sector had grown to significantly larger sizes with more embryos developed using a co-culture procedure according to the present invention.

EXAMPLE 14

Restoration of Fertility of Transgenic Plants

Figure 15:
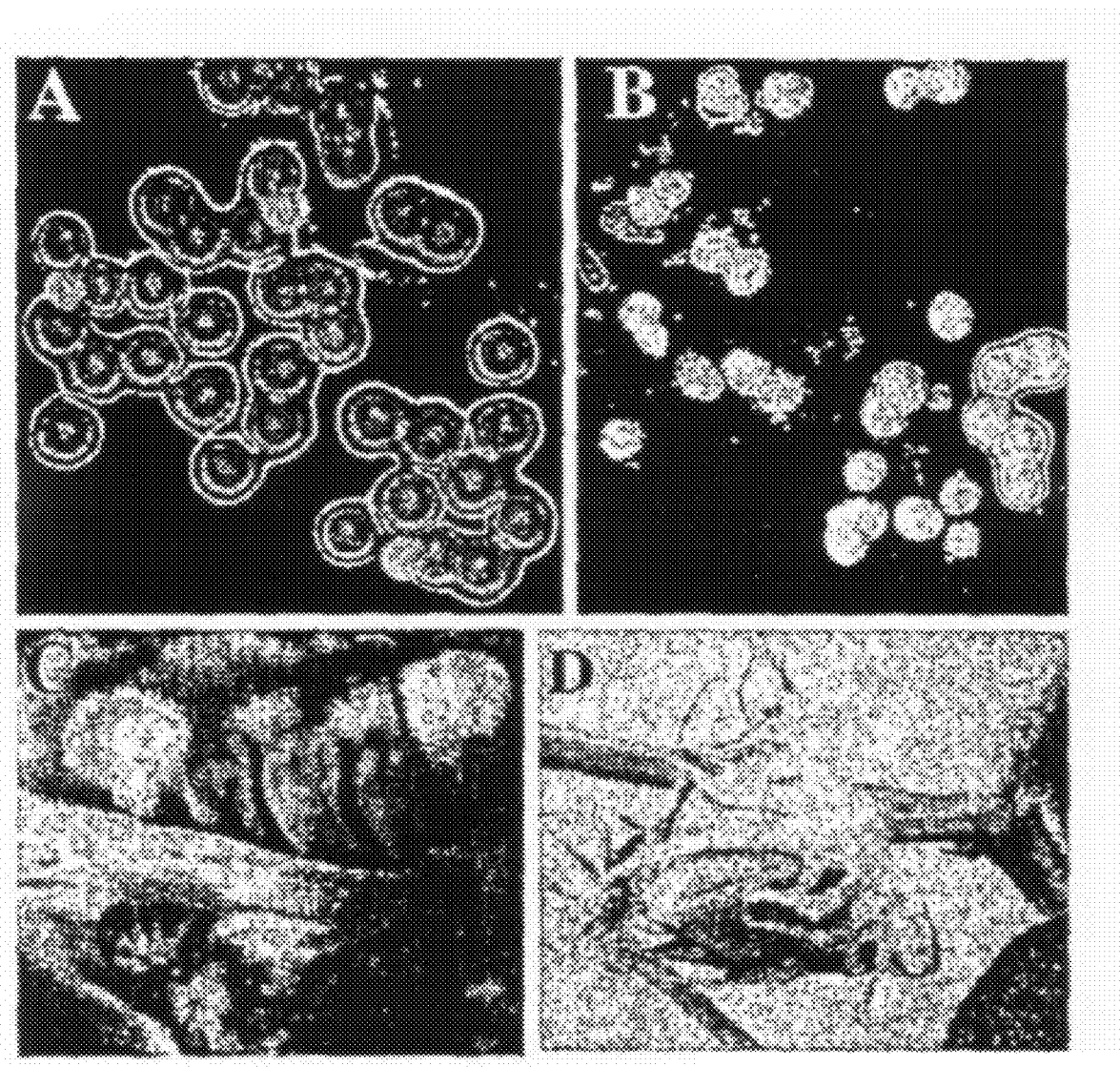
FIGS. 15A-15D show fresh pollens taken from wildtype (Coker 312) plants.

Self-fertile transgenic plants were obtained with the methods disclosed herein, although some defects in pollen development were seen (FIG. 15). Consequently, manual pollination may be preferred to produce seeds. The majority of plants from S16 were fertile when pollinated by pollens of plants derived from seed (FIG. 15). This can be an advantage, as backcrossing is often required to produce a commercial variety.

Abbreviations and terms used herein:
MS salt (Murashige and Skoog, 1962):
    332.02 mg/l $CaCl_2$
    170 mg/l $KH_2PO_4$
    1900 mg/l $KNO_3$
    180.54 mg/l $MgSO_4$
    128.4 mg/l $NaH_2PO_4$
    1650 mg/l $NH_4NO_3$
    0.025 mg/l $CoCl_2.6H_2O$
    0.025 mg/l $CuSO_4.5H_2O$
    36.7 mg/l FeNaEDTA
    6.20 mg/l $H_3BO_4$
    0.83 mg/l KI
    16.9 mg/l $MnSO_4.H_2O$
    0.25 mg/l $Na_2MoO_4.2H_2O$
    8.60 mg/l $ZnSO_4.7H_2O$
B5 vitamins
    100 mg/l myo-inositol
    1 mg/l nicotinic acid
    1 mg/l pyridoxine HCl,
    10 mg/l thiamine HCl SGM: Half-strength MS salt and half strength B5 Vitamins, 0.02 mg/l NAA, 0.1 mg/l MET (multi-effect trizazole), 5 g/l glucose, 2 g/l phytogel, pH 6.0

SM1: MS salt, B5 vitamins, 0.1 mg/l Kinetin, 0.05 mg/l 2,4-D, 30 g/l glucose, 2 g/l phytogel, pH 6.2

SM2: MS salt, B5 Vitamins, 1.9 g/l $KNO_3$, 30 g/l glucose; 2.5 µl phytogel, pH 6.4

LM1: MS salt, B5 Vitamins, 1.9 g/l $KNO_3$, 0.01 mg/l NAA, 30 g/l glucose, pH 6.4

LM2: MS salt with no $NH_4NO_3$, B5 Vitamins, 1.9 g/l $KNO_3$, 0.01 mg/l NAA, 30 g/l glucose, 1 g/l glutamine, 0.5 g/l asparagine, pH 6.4

LM3: MS salt, B5 Vitamins, 0.05 mg/l NAA, 30 g/l glucose, pH 6.4

LM4: MS salt, B5 Vitamins, 0.01 mg/l NAA, 0.5 mg/l picloram, 30 g/l glucose, pH 6.4

C1
  2.05 g/l $K_2HPO_4$
  1.45 g/l $KH_2PO_4$
  0.6 g/l $MgSO_4$-$7H_2O$
  0.5 g/l $(NH_4)_2SO_4$
  0.5 g/l $NH_4NO_3$
  0.01 g/l $CaCl_2$
  2 g/l glucose)
  0.5 mg/l $ZnSO_4$-$7H_2O$
  0.5 mg/l $CuSO_4$-$5H_2O$
  0.5 mg/l $H_3BO_3$
  0.5 mg/l $MnSO_4$—$H_2O$
  0.5 mg/l $NaMbO_4$-$2H_2O$
  1 mg/l $FeSO_4$
  B5 Vitamins
  0.01 mg/l NAA
  0.5 mg/l picloram
  40 mM MES
  0.5% glycerol
  0-100 µM acetosyringone
  pH 5.7-6.0

CP1: C1, plus 4 g/l phytogel.

R1: MS salt, B5 Vitamins, 1.9 g/l $KNO_3$, 30 g/L glucose, pH6.4, 2.8 g/l phytogel.

R2: MS salt with no $NH_4NO_3$, B5 Vitamins, 1.9 g/l $KNO_3$, 30 g/l, glucose, 1 g/l glutamine, 0.5 g/l asparagine, pH 6.4, 2.8 g/l phytogel R3: MS, B5 vitamins, 30 g/l glucose, 0.01 mg/l NAA, 3 g/l phytogel, pH 6.4

R4: Half-strength MS, B5 vitamins

MinAB
  2.05 g/l $K_2HPO_4$
  1.45 g/l $KH_2PO_4$
  0.6 g/l $MgSO_4$-$7H_2O$
  0.3 g/l NaCl
  0.5 g/l $(NH_4)_2SO_4$
  0.5 g/l $NH_4NO_3$
  0.01 g/l $CaCl_2$
  2 g/l glucose
  0.5 mg/l $ZnSO_4$-$7H_2O$
  0.5 mg/l $CuSO_4$-$5H_2O$
  0.5 mg/l $H_3BO_3$
  0.5 mg/l $MnSO_4$—$H_2O$
  0.5 mg/l $MbO_4$-$2H_2O$,
  1 mg/l $FeSO_4$
  pH7.0

IM
  1.05 g/l $K_2HPO_4$
  1.45 g/l $KH_2PO_4$
  0.6 µl $MgSO_4$-$7H_2O$
  0.3 g/l NaCl
  0.5 g/l $(NH_4)_2SO_4$
  0.5 g/l $NH_4NO_3$
  0.01 g/l $CaCl_2$,
  0.5 mg/l $ZnSO_4$-$7H_2O$
  0.5 mg/l $CuSO_4$-$5H_2O$
  0.5 mg/l $H_3BO_3$
  0.5 mg/l $MnSO_4$—$H_2O$
  0.5 mg/l $NaMbO_4$-$2H_2O$,
  1 mg/l $FeSO_4$
  0.5% glycerol
  2 g/l glucose
  100-200 µM acetosyringone
  40 mM MES
  pH5.7

BIBLIOGRAPHY

Ashby et al. (1988). *J. Bacteriol.* 170: 4181-4187.
Bayley et al. (1992). *Theoretical and Applied Genetics* 83: 645-649.
Bolten et al. (1986). *Science* 232: 983-985.
Bundock et al. (1995). *EMBO J.* 1995, 14:3206-14.
Chair, H. et al. (1997). *Kasetsart J.*, vol. 33, pp. 149-156.
Chen and Winans (1991). *J. Bacteriol.* 173: 1139-1144).
Cousins, Y. L. et al. (1991). *Aust. J. Plant Physiol.* 18: 481-494.
Davidonis, G. H. and Hamilton, R. H. (1983). *Plant Sci. Lett.* 32: 89-93.
de Groot et al. (1998). *Nat. Biotechol.*, 16:839-42.
Finer, J. (1988). *Plant Cell Rep.* 7: 399-402.
Finer and McMullen (1990). *Plant Cell Reports*, i:586-589.
Firoozabady et al. (1987). *Plant Molecular Biol.* 10: 105-116.
Fullner and Nester (1996). *J. Bacteriol.* 178:1498-504.
Hansen et al. (1994). *Proc. Nat'l Acad. Sci.* 91:7603-7607.
Hoshino et al. (1988). *Plant Biotech.* 15(I). 29-33.
Levee et al. (1999). *Molecular Breeding*, 5:429-440.
McCabe and Martinell (1993). *Bio/Technology* 11:596-598.
McLean (1994). *J. Biol. Chem.* 269:2645-2651.
Murashige and Skoog (1962). *Physiol. Plant*, 15:473.
Murray et al. (1993). *Transgenic Plants*, vol. 2, pp. 153-168.
Otani et al. (1998). *Plant Biotech*, vol. 15, pp. 11-16.
Owens et al. (1988). *Plant Physiol.* vol. 88, pp. 570-573.
Piers et al. (1996). *PNAS*, 93:1613-1618.
Rogowsky et al. (1987). *J Bacteriol.* 169:5101-12.
Sagare et al. (2000). *Plant Sci.* 160:139-147.
Scheeren-Groot et al. (1994). *J. Bacteriol.* 176: 6418-6246.
Sheikholeslam and Weeks (1987). *Plant Mol. Biol.*, vol. 8, pp. 291-298.
Schilperoort, R. A. et al. (1990). Process for the incorporation of foreign DNA into the genome of dicotyledonous plants. U.S. Pat. No. 4,940,838.
Schilperoort, R. A. et al. (1995). Process for the incorporation of foreign DNA into the genome of dicotyledonous plants. U.S. Pat. No. 5,464,763.
Stachel et al. (1985). *Nature*, 318: 624-629.
Still et al. (1976). *J. Amer. Soc. Hort. Sci.*, vol. 101, pp. 34-37.
Tokuji and Kuriyama (2003). *J. Plant Physiol.* 160:133-41.
Trolinder, N. L. and Goodin, J. E. (1987). *Plant Cell Reports* 6: 231-4.
Umbeck et al. (1987). *Bio/Technology* 5:263-266.
Veluthambi et al. (1989). *J. Bacteriol.* 171:3696-3703.
Vernade et al. (1988). *J. Bacteriol* 170: 5822-5829.
Walkerpeach, C. R. and Velten, J. (1994). *Plant Mol. Biol. Manual*, B1: 1-19.
Xing, D. et al. (1999). *Chin. J. Biotechnol.* 15:59-64.

What is claimed is:

1. A method for producing a transgenic cotton plant, said method comprising:
   (a) providing a proembryogenic cotton cell;
   (b) culturing the proembryogenic cell in a liquid medium to produce a cell suspension culture;
   (c) providing a culture of preinduced *Agrobacterium tumefaciens* that harbors a vector comprising an exogenous gene and a selectable marker, the *Agrobacterium* being capable of effecting the stable transfer of the exogenous gene and selectable marker to the genome of a plant cell, wherein the preinduced *Agrobacterium tumefaciens* is preinduced for virulence;
   (d) mixing a portion of the cell suspension culture and a portion of the *Agrobacterium* culture;
   (e) co-culturing the mixture of the cell suspension culture and the *Agrobacterium* culture on a porous solid support in contact with a co-culture medium for 1-5 days under continuous light to produce a population of cells some of which have been transformed with the exogenous gene and the selectable marker;
   (f) selecting cells that express the exogenous gene from the population of cells; and
   (g) transferring the selected cells onto at least one regeneration medium comprising zeatin, wherein said cells regenerate into a transgenic cotton plant by somatic embryogenesis.

2. The method of claim 1, wherein the proembryogenic cell is derived from callus.

3. The method of claim 1, wherein said solid support is selected from the group consisting of a membrane and a filter.

4. The method of claim 1, wherein the porous solid support comprises at least one of nylon, nitrocellulose, cellulose, and glass fibers.

5. The method of claim 1, wherein the cotton is a member selected from the group consisting of *Gossypium hirsutum* and *Gossypium barbadense*.

6. The method of claim 1, wherein the *Agrobacterium* is preinduced by culturing the *Agrobacterium* in the presence of a virulence inducing agent.

7. The method of claim 1, wherein the *Agrobacterium* is preinduced by culturing *Agrobacterium* that constitutively expresses an active virA mutant.

8. The method of claim 1, wherein the proembryogenic cotton cell is obtained by:
   obtaining an explant from a cotton plant;
   inducing callus formation from the explant; and
   generating proembryogenic tissue from the callus.

9. The method of claim 8, wherein the proembryogenic tissue is generated from the callus by initiating somatic embryogenesis of the callus.

10. The method of claim 8, wherein the proembryogenic tissue is generated from the callus by inducing differentiation of the callus.

11. The method of claim 8, wherein the explant is obtained by:
    sterilizing a cotton seed; and
    germinating the cotton seed to generate plant tissue for use as an explant.

12. The method of claim 11, wherein the plant tissue is a root or a shoot tip.

13. The method of claim 1, wherein the solid support is in contact with the co-culture medium by soaking the solid support in a liquid co-culture medium.

14. The method of claim 1, wherein the solid support is in contact with the co-culture medium by being laid on top of a solid co-culture medium.

15. The method of claim 1, wherein the co-culture medium in step (e) comprises MinAB salts, B5 vitamins, acetosyringone, glucose and glycerol.

16. The method of claim 1, wherein the co-culture medium in step (e) comprises MS salts, B5 vitamins, acetosyringone, glucose and glycerol.

17. The method of claim 1, further comprising backcrossing the transgenic cotton plant with a cotton germplasm of interest.

* * * * *